(12) United States Patent
Ivanko

(10) Patent No.: US 10,154,843 B2
(45) Date of Patent: *Dec. 18, 2018

(54) SURGICAL FASTENER APPLYING APPARATUS WITH CONTROLLED BEAM DEFLECTION

(71) Applicant: Covidien LP, Mansfield, MA (US)

(72) Inventor: David Ivanko, San Diego, CA (US)

(73) Assignee: Covidien LP, Mansfield, MA (US)

( * ) Notice: Subject to any disclaimer, the term of this patent is extended or adjusted under 35 U.S.C. 154(b) by 372 days.

This patent is subject to a terminal disclaimer.

(21) Appl. No.: 14/990,032

(22) Filed: Jan. 7, 2016

(65) Prior Publication Data

US 2016/0192935 A1  Jul. 7, 2016

Related U.S. Application Data

(63) Continuation of application No. 14/180,736, filed on Feb. 14, 2014, now Pat. No. 9,241,711, which is a continuation of application No. 13/625,153, filed on Sep. 24, 2012, now Pat. No. 8,701,961, which is a continuation of application No. 13/195,898, filed on Aug. 2, 2011, now Pat. No. 8,292,149, which is a
(Continued)

(51) Int. Cl.
| | |
|---|---|
| A61B 17/10 | (2006.01) |
| A61B 17/072 | (2006.01) |
| A61B 17/068 | (2006.01) |
| A61B 17/29 | (2006.01) |

(52) U.S. Cl.
CPC .......... *A61B 17/105* (2013.01); *A61B 17/068* (2013.01); *A61B 17/07207* (2013.01); *A61B 2017/07214* (2013.01); *A61B 2017/2926* (2013.01)

(58) Field of Classification Search
CPC .... A61B 17/068; A61B 17/072; A61B 17/105
USPC .......................... 227/19, 175.1, 176.1, 180.1
See application file for complete search history.

(56) References Cited

U.S. PATENT DOCUMENTS

| | | |
|---|---|---|
| 960,300 A | 6/1910 | Fischer |
| 2,301,622 A | 11/1942 | Hambrecht |
| (Continued) | | |

FOREIGN PATENT DOCUMENTS

| | | |
|---|---|---|
| EP | 0514185 A1 | 11/1992 |
| EP | 0625335 A1 | 11/1994 |
| (Continued) | | |

OTHER PUBLICATIONS

European Search Report for EP 12193587.8 date of completion is Feb. 6, 2013 (8 pages).
(Continued)

*Primary Examiner* — Nathaniel Chukwurah

(57) ABSTRACT

A surgical fastener applying apparatus including an anvil half-section having a distal end and a longitudinal axis; a cartridge receiving half-section having a distal end and operatively couplable with the anvil half-section such that the distal ends of the half-sections are in juxtaposed relation; and a deflection control system operatively engaged with and reinforcing the distal end of the anvil half-section when a force is applied to the distal end of the anvil half-section in a direction transverse to the longitudinal axis.

8 Claims, 12 Drawing Sheets

Related U.S. Application Data continuation of application No. 12/726,608, filed on Mar. 18, 2010, now Pat. No. 8,011,552, which is a continuation of application No. 12/358,332, filed on Jan. 23, 2009, now Pat. No. 7,699,205, which is a continuation of application No. 11/933,624, filed on Nov. 1, 2007, now Pat. No. 7,543,729, which is a continuation of application No. 10/958,074, filed on Oct. 4, 2004, now Pat. No. 7,296,722.

(60) Provisional application No. 60/512,497, filed on Oct. 17, 2003.

(56) References Cited

U.S. PATENT DOCUMENTS

| | | |
|---|---|---|
| 2,853,074 A | 9/1958 | Olson |
| 2,874,384 A | 2/1959 | Krone |
| 2,891,250 A | 6/1959 | Hirata |
| 3,079,606 A | 3/1963 | Bobrov et al. |
| 3,080,564 A | 3/1963 | Strekopov et al. |
| 3,252,643 A | 5/1966 | Strekopov et al. |
| 3,269,630 A | 8/1966 | Fleischer |
| 3,275,211 A | 9/1966 | Hirsch et al. |
| 3,278,107 A | 10/1966 | Rygg |
| 3,315,863 A | 4/1967 | O'Dea |
| 3,499,591 A | 3/1970 | Green |
| 3,589,589 A | 6/1971 | Akopov |
| 3,598,299 A | 8/1971 | Johnson |
| 3,692,224 A | 9/1972 | Astafiev et al. |
| 3,696,412 A | 10/1972 | Swanson |
| 3,795,034 A | 3/1974 | Strekopytov et al. |
| 3,889,683 A | 6/1975 | Kapitanov et al. |
| 3,935,981 A | 2/1976 | Akopov et al. |
| 3,949,923 A | 4/1976 | Akopov et al. |
| 3,973,709 A | 8/1976 | Akopov et al. |
| 4,047,654 A | 9/1977 | Alvarado |
| 4,111,206 A | 9/1978 | Vishnevsky et al. |
| 4,162,678 A | 7/1979 | Fedotov et al. |
| 4,216,890 A | 8/1980 | Akopov et al. |
| 4,216,891 A | 8/1980 | Behlke |
| 4,272,002 A | 6/1981 | Moshofsky |
| 4,290,542 A | 9/1981 | Fedotov et al. |
| 4,296,881 A | 10/1981 | Lee |
| 4,316,468 A | 2/1982 | Klieman et al. |
| 4,317,105 A | 2/1982 | Sinha et al. |
| 4,325,376 A | 4/1982 | Klieman et al. |
| 4,378,901 A | 4/1983 | Akopov et al. |
| 4,397,311 A | 8/1983 | Kanshin et al. |
| 4,442,964 A | 4/1984 | Becht |
| 4,453,661 A | 6/1984 | Genyk et al. |
| 4,470,533 A | 9/1984 | Schuler |
| 4,477,007 A | 10/1984 | Foslien |
| 4,485,811 A | 12/1984 | Chernousov et al. |
| 4,527,724 A | 7/1985 | Chow et al. |
| 4,550,870 A | 11/1985 | Krumme et al. |
| 4,570,633 A | 2/1986 | Golden |
| 4,585,153 A | 4/1986 | Failla et al. |
| 4,596,351 A | 6/1986 | Fedotov et al. |
| 4,605,001 A | 8/1986 | Rothfuss et al. |
| 4,607,636 A | 8/1986 | Kula et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,648,542 A | 3/1987 | Fox et al. |
| 4,684,051 A | 8/1987 | Akopov et al. |
| 4,741,336 A | 5/1988 | Failla et al. |
| 4,784,137 A | 11/1988 | Kulik et al. |
| 4,805,823 A | 2/1989 | Rothfuss |
| 4,848,637 A | 7/1989 | Pruitt |
| 4,863,088 A | 9/1989 | Redmond et al. |
| 4,892,244 A | 1/1990 | Fox et al. |
| 4,930,503 A | 6/1990 | Pruitt |
| 4,991,764 A | 2/1991 | Mericle |
| 5,005,754 A | 4/1991 | Van Overloop |
| 5,018,657 A | 5/1991 | Pedlick et al. |
| 5,065,929 A | 11/1991 | Schulze et al. |
| 5,074,454 A | 12/1991 | Peters |
| 5,083,695 A | 1/1992 | Foslien et al. |
| 5,111,987 A | 5/1992 | Moeinzadeh et al. |
| 5,129,570 A | 7/1992 | Schulze et al. |
| 5,137,198 A | 8/1992 | Nobis et al. |
| 5,141,144 A | 8/1992 | Foslien et al. |
| 5,170,925 A | 12/1992 | Madden et al. |
| 5,172,845 A | 12/1992 | Tejeiro |
| 5,180,092 A | 1/1993 | Crainich |
| 5,188,274 A | 2/1993 | Moeinzadeh et al. |
| 5,205,459 A | 4/1993 | Brinkerhoff et al. |
| 5,240,163 A | 8/1993 | Stein et al. |
| 5,263,629 A | 11/1993 | Trumbull et al. |
| RE34,519 E | 1/1994 | Fox et al. |
| 5,275,322 A | 1/1994 | Brinkerhoff et al. |
| 5,275,323 A | 1/1994 | Schulze et al. |
| 5,285,945 A | 2/1994 | Brinkerhoff et al. |
| 5,292,053 A | 3/1994 | Bilotti et al. |
| 5,307,976 A | 5/1994 | Olson et al. |
| 5,312,024 A | 5/1994 | Grant et al. |
| 5,332,142 A | 7/1994 | Robinson et al. |
| 5,344,061 A | 9/1994 | Crainich |
| 5,364,003 A | 11/1994 | Williamson, IV |
| 5,376,095 A | 12/1994 | Ortiz |
| 5,381,943 A | 1/1995 | Allen et al. |
| 5,383,880 A | 1/1995 | Hooven |
| 5,395,033 A | 3/1995 | Byrne et al. |
| 5,395,034 A | 3/1995 | Allen et al. |
| 5,397,324 A | 3/1995 | Carroll et al. |
| 5,405,073 A | 4/1995 | Porter |
| 5,415,334 A | 5/1995 | Williamson et al. |
| 5,415,335 A | 5/1995 | Knodell, Jr. |
| 5,417,361 A | 5/1995 | Williamson, IV |
| 5,431,323 A | 7/1995 | Smith et al. |
| 5,433,721 A | 7/1995 | Hooven et al. |
| 5,439,156 A | 8/1995 | Grant et al. |
| 5,447,265 A | 9/1995 | Vidal et al. |
| 5,452,836 A | 9/1995 | Huitema et al. |
| 5,452,837 A | 9/1995 | Williamson, IV et al. |
| 5,458,279 A | 10/1995 | Plyley |
| 5,465,894 A | 11/1995 | Clark et al. |
| 5,465,895 A | 11/1995 | Knodel et al. |
| 5,470,007 A | 11/1995 | Plyley et al. |
| 5,470,010 A | 11/1995 | Rothfuss et al. |
| 5,484,451 A | 1/1996 | Akopov et al. |
| 5,485,947 A | 1/1996 | Olson et al. |
| 5,487,500 A | 1/1996 | Knodel et al. |
| 5,489,058 A | 2/1996 | Plyley et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,937 A | 7/1996 | Boiarski et al. |
| 5,547,117 A | 8/1996 | Hamblin et al. |
| 5,549,628 A | 8/1996 | Cooper et al. |
| 5,551,622 A | 9/1996 | Yoon |
| 5,553,765 A | 9/1996 | Knodel et al. |
| 5,562,239 A | 10/1996 | Boiarski et al. |
| 5,562,241 A | 10/1996 | Knodel et al. |
| 5,564,615 A | 10/1996 | Bishop et al. |
| 5,575,803 A | 11/1996 | Cooper et al. |
| 5,580,067 A | 12/1996 | Hamblin et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,609,285 A | 3/1997 | Grant et al. |
| 5,624,452 A | 4/1997 | Yates |
| 5,630,541 A | 5/1997 | Williamson, IV et al. |
| 5,632,432 A | 5/1997 | Schulze et al. |
| 5,632,433 A | 5/1997 | Grant et al. |
| 5,634,584 A | 6/1997 | Okorocha et al. |
| 5,641,111 A | 6/1997 | Ahrens et al. |

(56) References Cited

U.S. PATENT DOCUMENTS

| | | |
|---|---|---|
| 5,655,698 A | 8/1997 | Yoon |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley et al. |
| 5,680,982 A | 10/1997 | Schulze et al. |
| 5,692,668 A | 12/1997 | Schulze et al. |
| 5,697,542 A | 12/1997 | Knodel et al. |
| 5,697,543 A | 12/1997 | Burdorff |
| 5,702,409 A | 12/1997 | Rayburn et al. |
| 5,704,534 A | 1/1998 | Huitema et al. |
| 5,716,366 A | 2/1998 | Yates |
| 5,725,554 A | 3/1998 | Simon et al. |
| 5,732,871 A | 3/1998 | Clark et al. |
| 5,735,848 A | 4/1998 | Yates et al. |
| 5,752,965 A | 5/1998 | Francis et al. |
| 5,762,255 A | 6/1998 | Chrisman et al. |
| 5,769,303 A | 6/1998 | Knodel et al. |
| 5,769,892 A | 6/1998 | Kingwell |
| 5,779,132 A | 7/1998 | Knodel et al. |
| 5,785,232 A | 7/1998 | Vidal et al. |
| 5,794,834 A | 8/1998 | Hamblin et al. |
| 5,797,537 A | 8/1998 | Oberlin et al. |
| 5,810,240 A | 9/1998 | Robertson |
| 5,810,811 A | 9/1998 | Yates et al. |
| 5,810,855 A | 9/1998 | Rayburn et al. |
| 5,820,009 A | 10/1998 | Melling et al. |
| 5,826,776 A | 10/1998 | Schulze et al. |
| 5,855,311 A | 1/1999 | Hamblin et al. |
| 5,871,135 A | 2/1999 | Williamson, IV et al. |
| 5,878,938 A | 3/1999 | Bittner et al. |
| 5,919,198 A | 7/1999 | Graves, Jr. et al. |
| 5,988,479 A | 11/1999 | Palmer |
| 6,010,054 A | 1/2000 | Johnson et al. |
| 6,045,560 A | 4/2000 | McKean et al. |
| 6,099,551 A | 8/2000 | Gabbay |
| 6,131,789 A | 10/2000 | Schulze et al. |
| 6,131,790 A | 10/2000 | Piraka |
| 6,202,914 B1 | 3/2001 | Geiste et al. |
| 6,264,087 B1 | 7/2001 | Whitman |
| 6,315,183 B1 | 11/2001 | Piraka |
| 6,325,810 B1 | 12/2001 | Hamilton et al. |
| 7,296,722 B2 | 11/2007 | Ivanko |
| 7,543,729 B2 | 6/2009 | Ivanko |
| 7,699,205 B2 | 4/2010 | Ivanko |
| 7,824,426 B2 | 11/2010 | Racenet et al. |
| 8,011,552 B2 * | 9/2011 | Ivanko .......... A61B 17/07207 227/175.1 |
| 8,701,961 B2 | 4/2014 | Ivanko |
| 9,241,711 B2 | 1/2016 | Ivanko |
| 2005/0222616 A1 | 10/2005 | Rethy et al. |

FOREIGN PATENT DOCUMENTS

| | | |
|---|---|---|
| EP | 0639349 A2 | 2/1995 |
| EP | 0878168 A1 | 11/1998 |
| EP | 1400206 A1 | 3/2004 |
| WO | 8200969 A1 | 4/1982 |
| WO | 02/30297 A2 | 4/2002 |
| WO | 03079909 A2 | 10/2003 |

OTHER PUBLICATIONS

Extended European Search Report for EP 04024382.6-2318 date of completion is Feb. 1, 2005; (5 pages).

European Office Action corresponding to counterpart Int'l Appln EP 12 193 587.8 dated Oct. 14, 2015.

European Examination Report dated Jan. 8, 2018 issued in corresponding EP Application No. 16186780.9.

Extended European Search Report for application No. 16 18 6780.9 dated Feb. 6, 2017.

* cited by examiner

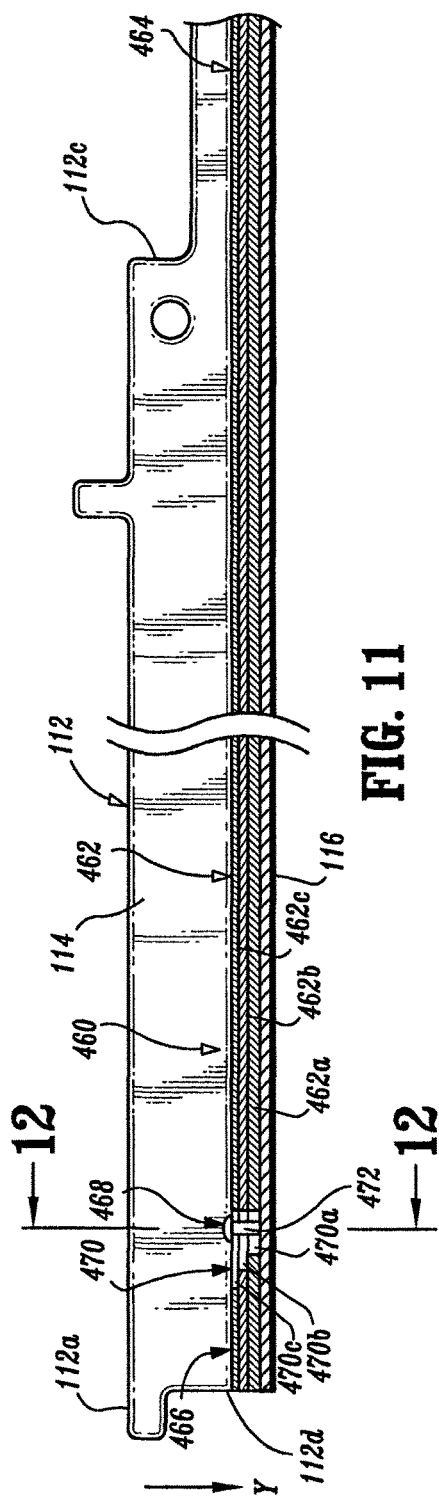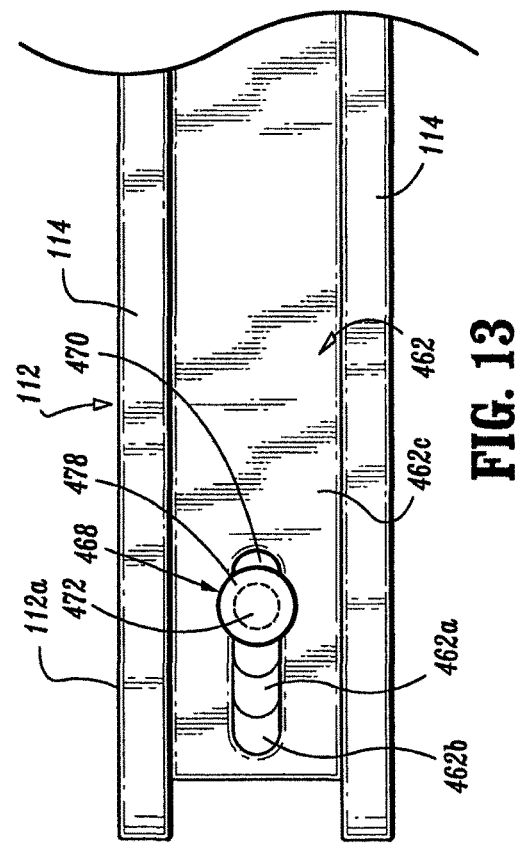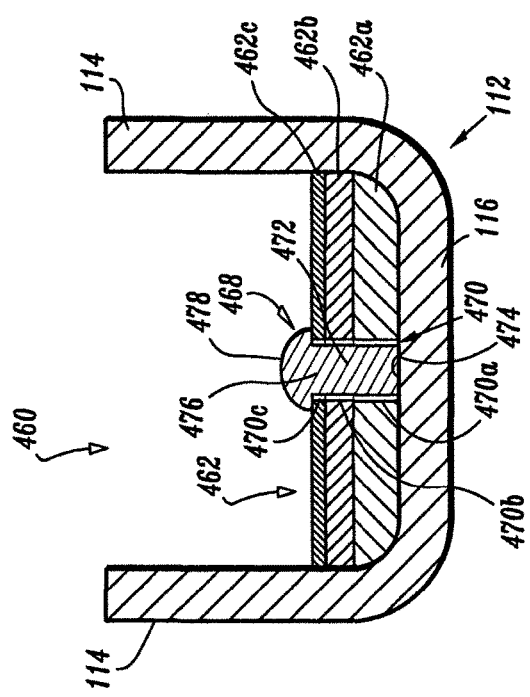
FIG. 11
FIG. 12
FIG. 13

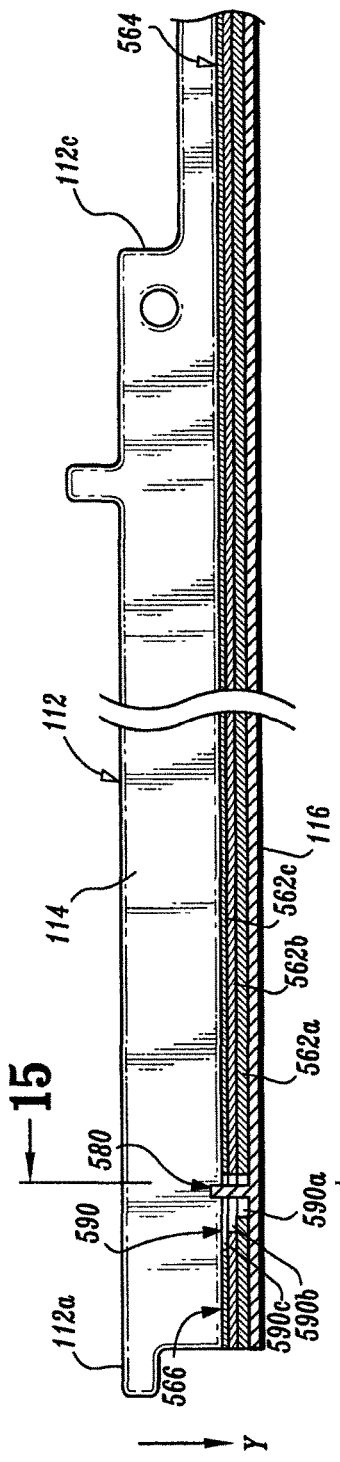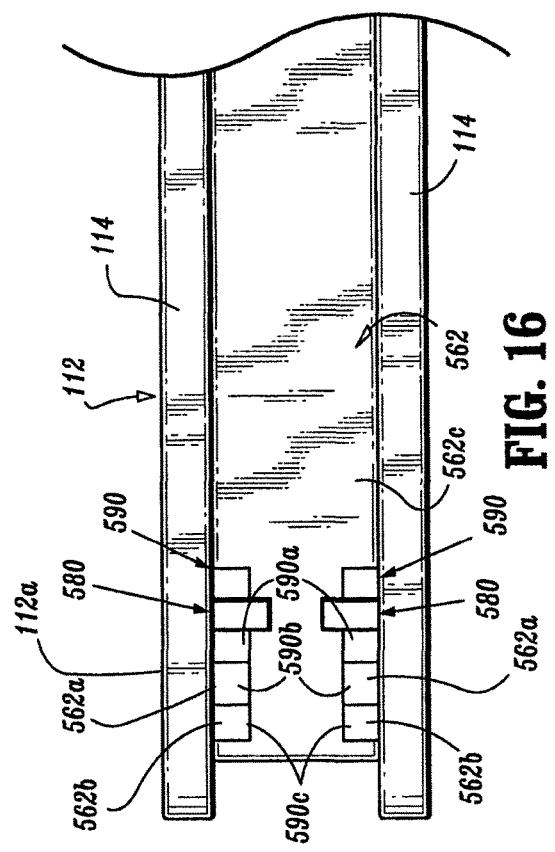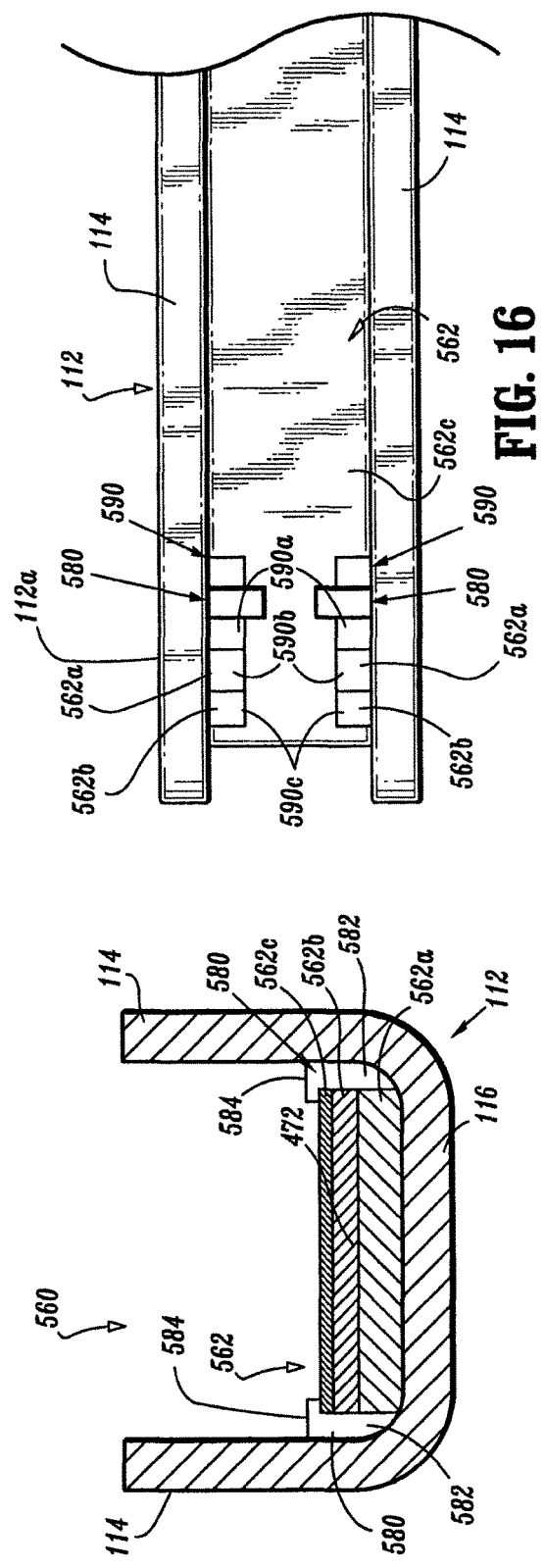
FIG. 14
FIG. 15
FIG. 16

SURGICAL FASTENER APPLYING APPARATUS WITH CONTROLLED BEAM DEFLECTION

CROSS REFERENCE TO RELATED APPLICATIONS

This application is a Continuation of U.S. patent application Ser. No. 14/180,736, filed Feb. 14, 2014 (now U.S. Pat. No. 9,241,711), which is a Continuation of U.S. patent application Ser. No. 13/625,153, filed Sep. 24, 2012 (now U.S. Pat. No. 8,701,967), which is a Continuation of U.S. patent application Ser. No. 13/195,898, filed Aug. 2, 2011 (now U.S. Pat. No. 8,292,149), which is a Continuation of U.S. patent application Ser. No. 12/726,608, filed Mar. 18, 2010 (now U.S. Pat. No. 8,011,552), which is a Continuation of U.S. patent application Ser. No. 12/358,332, filed Jan. 23, 2009 (now U.S. Pat. No. 7,699,205), which is a Continuation of U.S. patent application Ser. No. 11/933,624, filed Nov. 1, 2007 (now U.S. Pat. No. 7,543,729), which is a Continuation of U.S. patent application Ser. No. 10/958,074, filed Oct. 4, 2004 (now U.S. Pat. No. 7,296,722), which claims benefit of U.S. Provisional Patent Application Ser. No. 60/512,497 filed Oct. 17, 2003, and the disclosures of each of the above-identified applications are hereby incorporated by reference in their entirety.

BACKGROUND

Technical Field

The present disclosure relates to surgical fastener applying apparatus and, more particularly, to surgical fastener applying apparatus that include a deflection control system for controlling and/or reducing the rate of deflection of an anvil beam.

Background of Related Art

Surgical fastener applying apparatus, for example, surgical stapling apparatus, have been developed in which a staple cartridge receiving half-section including a staple cartridge assembly provided at a distal end thereof, is operatively connected (e.g., pivotably connected) to an anvil half-section including an anvil provided at a distal end thereof. The staple cartridge assembly preferably includes a plurality of surgical staples which are ejectable therefrom. The staple cartridge assembly may be manufactured as an integral part of the staple cartridge receiving half-section, or the staple cartridge assembly may be designed and manufactured as a disposable loading unit for use in a reusable surgical stapling apparatus.

Typically, when the distal end of the staple cartridge receiving half-section is approximated toward the distal end of the anvil half-section, to clamp tissue inserted therebetween in preparation for stapling, the opposing surfaces of the distal end of the staple cartridge assembly and the distal end of the anvil assembly are spaced apart by a predetermined distance which is pre-established and fixed for each surgical stapling apparatus. This spacing is sometimes referred to as the "tissue gap" of the surgical stapling apparatus.

Since it is desirable that the "tissue gap" be substantially uniform and/or "fixed" (i.e., having the same dimension throughout the stapling operation), in order to form lines of uniform staples along the cartridge, the operator of the surgical stapling apparatus needs to ascertain whether the "tissue gap" is loaded with more or thicker tissue than recommended (i.e., overloaded) which may result in undesired or increased deflection of the distal end of the anvil half-section and/or the staple cartridge receiving half-section. As used herein, the term "deflection" is understood to include flexing, bending, deforming, biasing, skewing and the like.

It is desirable that tissue having a thickness larger, preferably slightly larger, than the height of the "tissue gap" be clamped between the tissue contacting surface of the staple cartridge assembly and the anvil so that when the surgical stapling apparatus is clamped onto the tissue, the tissue substantially fills the entire height of the "tissue gap". However, it has been noticed that clamping of such tissue between the tissue contacting surfaces of the distal ends of the anvil and staple cartridge receiving half-sections tends to cause the distal ends of the anvil and/or staple cartridge receiving half-sections to deflect. The greater the initial and/or resultant thickness of tissue clamped between the distal ends of the staple cartridge receiving and anvil half-section, especially adjacent and at their distal tips, the greater the degree of deflection of the distal end of the anvil half-section and/or the staple cartridge receiving half-section.

In the past, the deflection at the distal end of the anvil half-section was reduced and/or eliminated by using a relatively heavier construction (i.e., thicker structural elements), a relatively larger construction or relatively stronger materials. These approaches increase the size and/or cost of the surgical stapling apparatus.

It would be desirable to provide a surgical stapling apparatus that includes a deflection control system for controlling and/or reducing the rate and/or degree of deflection of the distal end of the anvil half-section when tissue is clamped between the distal ends of the anvil and staple cartridge receiving half-sections.

It would also be desirable to provide a surgical stapling apparatus that has a deflection control system which allows rapid initial deflection of the distal end of the anvil half-section to a specific value and which thereafter causes a decrease or reduction in the rate and/or degree of deflection in a predetermined manner.

It would also be desirable to provide a surgical stapling apparatus that includes a deflection control system which allows rapid initial deflection of the distal end of the anvil half-section to efficaciously achieve the optimal tissue gap when clamping relatively thin tissue and which thereafter reduces the rate of deflection in relatively thicker tissue to maintain the tissue gap as close as possible to the optimal tissue gap.

Surgical stapling apparatus constructed in this manner would allow for rapid deflection of the distal end of the anvil half-section to a specific value followed by a decrease in the rate of deflection of the same. Accordingly, the distal end of the anvil half-section is able to deflect quickly to the optimal tissue gap in relatively thin tissue and deflect slowly in relatively thicker tissue to remain as close as possible to the optimal tissue gap.

SUMMARY

According to an aspect of the present disclosure, a surgical fastener applying apparatus is provided including an anvil half-section including a distal end and a proximal end defining a longitudinal axis, a cartridge receiving half-section including a distal end, and a deflection control system operatively associated with the anvil half-section. The cartridge receiving half-section is desirably operatively couplable with the anvil half-section such that the distal end of the anvil half-section is movable into juxtaposed relation to the distal end of the cartridge receiving half-section. A tissue gap is defined between the distal end of the anvil half-section and the distal end of the cartridge receiving half-section when the anvil and cartridge half-sections are coupled together.

The deflection control system is configured and adapted to reinforce the distal end of the anvil half-section when a force is applied there in a direction transverse to the longitudinal axis.

In addition, the anvil half-section defines a tissue contacting surface. Accordingly, the deflection control system reinforces the distal end of the anvil half-section when a force is applied to the distal end of the anvil half-section in a direction transverse to the longitudinal axis and normal to a plane defined by the tissue contacting surface of the anvil half-section.

In one embodiment, the anvil half-section includes a U-shaped channel member having a pair of side walls interconnected by a base wall. In this embodiment, the deflection control system is operatively associated with the channel member. The deflection control system is desirably operatively disposed within the channel member.

According to one embodiment, the deflection control system can include a U-shaped channel section having a pair of side walls interconnected by a base wall. Preferably, the base wall of the channel section of the deflection control system is adjacent, more preferably in contact with the base wall of the channel member of the anvil half-section, and the side walls of the channel section are disposed interior of and adjacent the side walls of the channel member. It is envisioned that each side wall of the pair of side walls of the channel section has a height which is less than a height of a respective one of the pair of side walls of the channel member thereby defining a reveal along each side wall of the pair of side walls of the channel member. Preferably, the relative height of each side wall of the pair of side walls of the channel section is uniform along a length thereof, and each side wall of the pair of side walls of the channel section preferably has a uniform thickness along a length thereof.

Desirably, at least a proximal end of the channel section is fixedly secured to a proximal end of the channel member.

It is envisioned that the deflection control system can be a multi-stage system, e.g., a two-stage system, a three-stage system, a four-stage system, etc. In a two-stage system, the deflection control system begins reducing the rate of deflection of the distal end of the channel member in a second stage of deflection. The second stage of deflection desirably takes effect when the reveal between the side walls of the channel member and the side walls of the channel section is about zero. Accordingly, the distal end of the channel member and the distal end of the channel section deflect concomitantly.

The deflection control system functions such that the greater the rate of deflection of the distal end of the channel member, the greater the reduction in the rate at which the distal end of the channel section deflects. It is contemplated that the reveal between the distal end of the channel member and the distal end of the channel section can be zero.

According to another embodiment of the present disclosure, the deflection control system can include a first U-shaped channel section having a pair of side walls interconnected by a base wall, wherein the base wall of the first channel section of the deflection control system is adjacent to or, more preferably in contact with the base wall of the channel member of the anvil half-section, and a second U-shaped channel section having a pair of side walls interconnected by a base wall, wherein the base wall of the second channel section of the deflection control system is adjacent to or, more preferably in contact with the base wall of the first channel section of the deflection control system.

A distal end of each side wall of the pair of side walls of the first channel section can have a height which is less than a height of a respective side wall of the pair of side walls of the channel member thereby defining a first reveal along each of the pair of side walls of the channel member. In addition, each side wall of the pair of side walls of the second channel section can have a height which is less than a height of the respective side walls of the pair of side walls of the first channel section thereby defining a second reveal along a distal end of each side wall of the pair of side walls of the second channel section.

A proximal end of each of the first and second channel sections can be operatively fixedly secured to a proximal end the channel member. It is contemplated that the height of the distal end of each side wall of the pair of side walls of the first channel section and the height of a corresponding distal end of each side wall of the pair of side walls of the second channel section are uniform along each of the lengths thereof.

In this embodiment the deflection control system is a three-stage system. In a three-stage system the deflection control system begins reducing the rate of deflection of the distal end of the channel section in a second stage of deflection, and in a third stage of deflection the deflection control system reduces the rate of deflection of the distal end of the channel member by an additional amount. In operation, the second stage of deflection engages when the first reveal between the side walls of the channel member and the side walls of the first channel section is about zero, whereby the distal end of the channel member and the distal end of the first channel section deflect concomitantly. The third stage of deflection engages when the second reveal between the side walls of the first channel section and the side walls of the second channel section is about zero, whereby the distal end of the channel member, the distal end of the first channel section and the distal end of the second channel section deflect concomitantly.

According to another embodiment the deflection control system includes a pair of reinforcing ribs each disposed along an inner surface of a respective side wall of the pair of side walls of the channel member. Each rib of the pair of reinforcing ribs of the deflection control system has a height which is less than the height of the respective side walls of the channel member thereby defining a reveal along each of the pair of side walls of the channel member. It is envisioned that a proximal end of each of the pair of reinforcing ribs is pinned to a portion of the proximal end of the channel member.

In another embodiment, a proximal end of the deflection control system is fixedly secured to a portion of the proximal end of the channel member and a portion of the distal end of the deflection control system is longitudinally slidingly coupled to the channel member. The deflection control system can include at least one, preferably a plurality of, reinforcing plate(s) adjacent, preferably in contact with the base wall of the channel member.

In this embodiment, the surgical fastener applying apparatus can further include a pin member fixedly secured to the base wall of the channel member. The distal end of each of the plurality of reinforcing plates is slidingly coupled to the channel member by the pin member extending through a plurality of elongate longitudinally oriented slots formed, one each, in the plurality of respective reinforcing plates. The elongate slots preferably increase in length from the reinforcing plate which is closest to the base wall of the channel member to the reinforcing plate which is furthest from the base wall of the channel member. The slots of the plates each have a proximal edge, and desirably the proximal edges are in registration with one another. The pin member desirably includes a head secured to an end thereof that is opposite to the base wall. The head engages the reinforcement plates and forces the distal end of each of the reinforcing plates to deflect concomitantly with the distal end of channel member.

In operation, as the distal end of the channel member and the deflection control system deflect in a direction transverse to the longitudinal axis, the distal end of at least one of the plurality of reinforcing plates translates in a longitudinal direction. The deflection control system is a multi-stage system which begins to incrementally reduce the rate of deflection of the distal end of the channel member as a distal end of each elongate slot of each respective reinforcing plate engages the pin member. The deflection control system incrementally reduces the rate at which the distal end of the channel member deflects.

In another embodiment, surgical fastener applying apparatus can be provided with a pair of juxtaposed shoulders each extending from an inner surface of the side walls of the channel member in a distal end thereof. Each reinforcing plate can include an elongate recesses formed along each lateral side thereof and in operative engagement with a respective one of the pair of shoulders. The elongate recesses preferably increase in length from the reinforcing plate which is closest to the base wall of the channel member to the reinforcing plate which is furthest from the base wall of the channel member. Each of the elongate recesses has a proximal edge and wherein the proximal edges are in registration with one another. Each shoulder preferably includes a head portion secured to an end thereof, the head portion being configured and dimensioned to force the distal end of each of the reinforcing plates to deflect concomitantly with the distal end of channel member.

In operation, as the distal end of the channel member and the deflection system deflect in a direction transverse to the longitudinal axis the distal end of each of the plurality of reinforcing plates translates in a longitudinal direction. The deflection control system is a multi-stage system, wherein the deflection control system begins to incrementally reduce the rate of deflection of the distal end of the channel member as a distal end of each elongate recess of each respective reinforcing plate engages a respective shoulder, the deflection control system incrementally reduces the rate at which the distal end of the channel member deflects.

According to another aspect of the present disclosure, a deflection control system is provided for a surgical fastener applying apparatus that includes an anvil half-section having a channel member and a cartridge receiving half-section operatively couplable to the anvil half-section. The deflection control system includes an elongate reinforcing assembly having a proximal end operatively engaged with a proximal end of the channel member and a distal end operatively associated with a distal end of the channel member, wherein the reinforcing assembly incrementally reduces deflection of the distal end of the channel member when forces are applied to the distal end of the channel member in a direction transverse to a longitudinal axis of the channel member and normal to a tissue contacting surface of the anvil half-section.

According to another aspect of the present disclosure, a surgical fastener applying apparatus is provided. It includes an anvil half-section including a distal end and a proximal end defining a longitudinal axis, the anvil half-section including a channel member having pair of juxtaposed side walls interconnected by a base wall, each side wall defining a through hole having a diameter. The apparatus further includes a cartridge receiving half-section including a distal end, wherein the cartridge receiving half-section is couplable with the anvil half-section such that the distal end of the anvil half-section is movable into juxtaposed relation to the distal end of the cartridge receiving half-section. The distal ends of the anvil and cartridge half-sections can be pivotable about a pivot axis transverse to the longitudinal axis.

The surgical fastener applying apparatus further includes a deflection control system operatively associated with the anvil half-section for reinforcing the distal end of the anvil half-section when a force is applied to the distal end of the anvil half-section in a direction transverse to the longitudinal axis. The deflection control system most preferably includes a pair of reinforcing ribs having a distal end and a proximal end. The distal end of each reinforcing rib is fixedly secured to an inner surface of a respective side wall of the pair of side walls of the channel member and the proximal end of each reinforcing rib extends beyond the pivot axis. The proximal end of each reinforcing rib defines a hole in registration with the through hole defined in the side walls of the channel member. The holes are desirably positioned proximal of the pivot axis. The deflection control system further includes a cam member extending through the holes formed in each side wall of the channel member and each reinforcing rib, the cam having a diameter smaller than the diameter of the through hole formed in each reinforcing rib to thereby define a reveal between each reinforcing rib and the cam member.

This deflection control system is a two-stage system. Accordingly, in operation, the deflection control system begins reducing the degree and the rate of deflection of the distal end of the channel member in a second stage of deflection. The second stage of deflection takes effect when the reveal between an upper portion of the hole formed in each reinforcing rib and an upper portion of the cam is zero.

Further features of the disclosure, its nature and various advantages will be more apparent from the accompanying drawings and the following detailed description.

BRIEF DESCRIPTION OF THE DRAWINGS

By way of example only, preferred embodiments of the present disclosure will be described herein with reference to the accompanying drawings, in which:

FIG. 11 is a longitudinal cross-sectional view of the distal end of an anvil half-section of a channel member in accordance with yet another alternative embodiment of the present disclosure;

FIG. 12 is a transverse cross-sectional view of a portion of the distal end of the channel member of FIG. 11, as would be seen along line 12-12 of FIG. 11;

FIG. 13 is a bottom plan view of a portion of the distal end of the channel member of FIGS. 11 and 12;

FIG. 14 is a longitudinal cross-sectional view of a portion of the distal end of a channel member of an anvil half-section in accordance with yet another alternative embodiment of the present disclosure;

FIG. 15 is a transverse cross-sectional view of a distal end portion of the channel member of FIG. 14, as would be seen along line 15-15 of FIG. 14;

FIG. 16 is a top plan view of a portion of the distal end of the channel member of FIGS. 14 and 15;

DETAILED DESCRIPTION OF PREFERRED EMBODIMENTS

Figure 1:
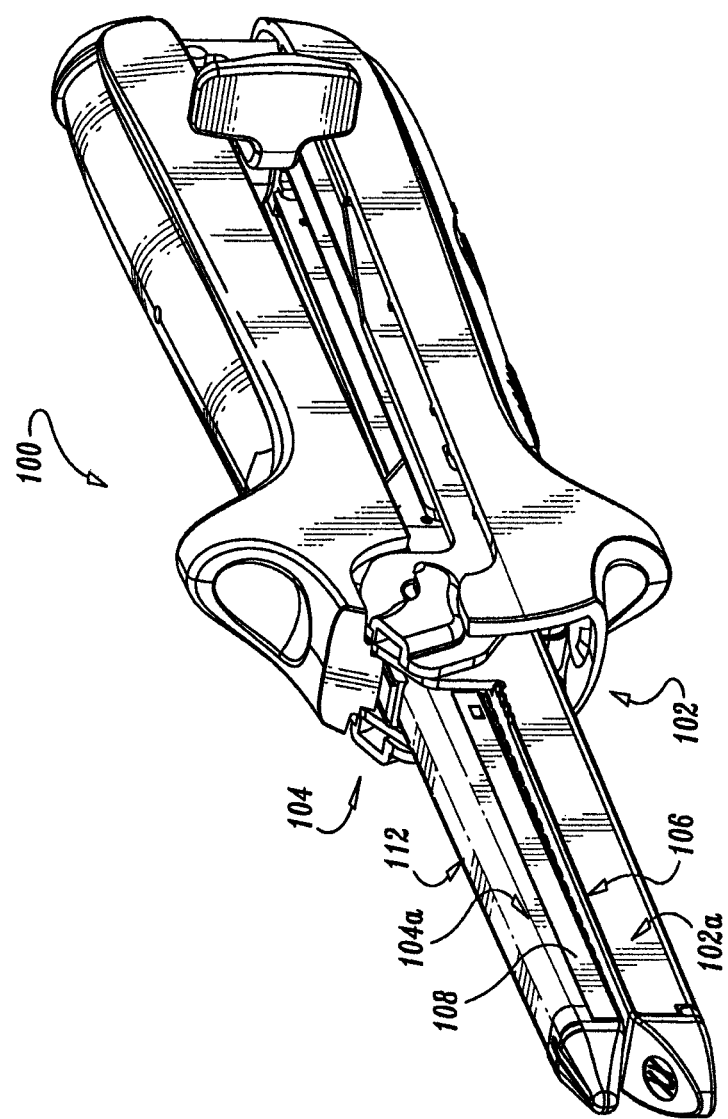
FIG. 1 is a perspective view of a surgical fastener applying apparatus in accordance with the present disclosure.

Preferred embodiments of the presently disclosed surgical fastener applying apparatus will now be described in detail with reference to the drawing figures wherein like reference numerals identify similar or identical elements. In the drawings and in the description which follows, the term "proximal" will refer to the end of the surgical fastener applying apparatus which is closest to the operator, while the term "distal" will refer to the end of the surgical fastener applying apparatus which is furthest from the operator.

Referring to FIGS. 1-5, a surgical fastener applying apparatus, in accordance with the present disclosure, is shown generally as 100. Apparatus 100 is particularly adapted to apply surgical staples and includes a cartridge receiving half-section 102, an anvil half-section 104 operatively coupled to cartridge receiving half-section 102, a staple cartridge assembly 106 fixedly or removably supported in a distal end 102a of cartridge receiving half-section 102 and an anvil plate 108 fixedly or removably supported on a distal end 104a of anvil half-section 104.

For purposes of illustration, the present disclosure describes beam deflection control systems with specific reference to a surgical fastener applying apparatus, preferably a surgical stapler. It is envisioned, however, that the beam deflection control system and illustrative embodiments herein may be incorporated in any surgical fastener applying apparatus having at least one cantilevered beam member which may be subject to deflection under an applied load which has a force component transverse to the longitudinal axis of the beam. It is further envisioned that the beam deflection control system and illustrative embodiments disclosed herein may be incorporated into and/or equally applied to endoscopic, laparoscopic as well as open type surgical instruments. The "beam" referred to in "beam deflection control system" can be distal end 102a of cartridge half-section 102, and/or distal end 104a of anvil half-section 104, although most of the discussion herein will refer to the distal end of the anvil half-section because, of the two, typically it is the member which deflects the most.

Figure 2:
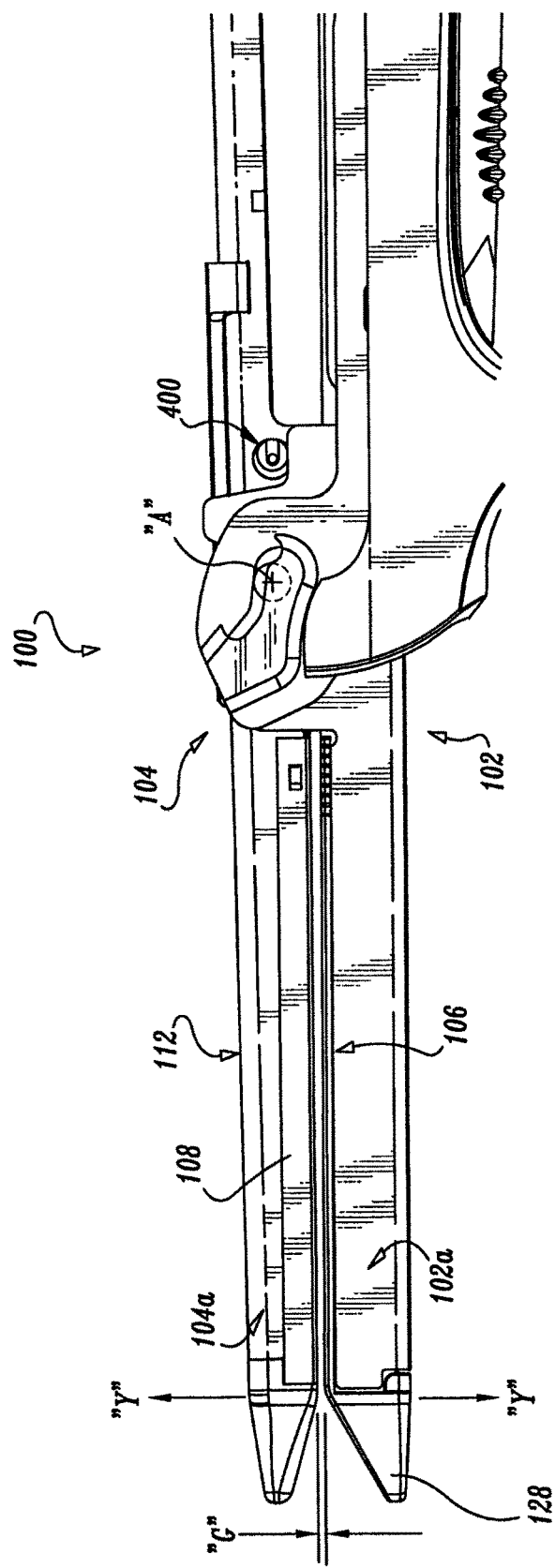
FIG. 2 is a side elevational view showing the distal end of the surgical fastener applying apparatus of FIG. 1.

As seen in FIG. 2, when anvil half-section 104 is operatively coupled to cartridge receiving half-section 102, a tissue gap "G" exists between distal end 104a of anvil half-section 104 and distal end 102a of cartridge receiving half-section 102. Tissue gap "G" is typically set to a predetermined dimension during the manufacture of surgical stapling apparatus 100 to allow for desired staple formation. Preferably, tissue gap "G" is tapered, i.e., narrower adjacent a distal end of apparatus 100 than at a location proximal of the distal end of apparatus 100. As described above with regard to previous surgical fastener applying apparatus, when distal ends 104a of anvil half-section 104 and distal end 102a of cartridge receiving half-section 102 are clamped onto tissue, a deflection force is exerted thereon, in the directions indicated by arrows "Y" (i.e., in directions transverse to the longitudinal axis of the surgical fastener applying apparatus), tending to cause distal end 104a of anvil half-section 104 and/or distal end 102a of cartridge receiving half-section 102 to deflect, e.g., in the direction of arrows "Y". As is known in the art, the degree of deflection of distal ends 104a, 102a of anvil half-section 104 and cartridge receiving half-section 102 tend to increase at locations or in portions increasingly closer to the distal tips thereof. As is also known in the art, the thicker the tissue to be clamped the greater the deflection force exerted. Also, tissue thickness can vary, e.g., increase, during approximation and stapling. This can be due, e.g., to tissue fluid flow typically toward the distal tip of the apparatus during approximation of distal ends 104a, 102a of anvil and cartridge receiving half-sections 104, 102, especially those that are pivotably mounted.

Thus, the greater the degree of deflection in the direction of arrows "Y", the greater the likelihood that the dimension of the distal end of tissue gap "G" may vary from its predetermined setting. As a result, it may occur that staples (not shown) fired from staple cartridge assembly 106 may form non-uniformly along the length of anvil plate 108. In the region where the dimension of tissue gap "G" remains or is close to the predetermined setting, i.e., near intermediate point 112c (FIG. 3) the legs of the staples will form as intended. However, it may occur that if excessively thick over-indicated tissue is inadvertently fastened, the dimension of tissue gap "G" may increase beyond its predetermined setting, e.g., near the distal tip of anvil plate 108, and there is a possibility that in that area the legs of the staples may not form as desired. The purpose of this disclosure is to reduce the possibility of or prevent this from occurring. Elsewise stated, the purpose of this disclosure is to increase the possibility that even if excessively thick over-indicated tissue is encountered, deflection will be minimized or prevented, to enhance the possibility of and provide for acceptable staple formation.

Figure 3:
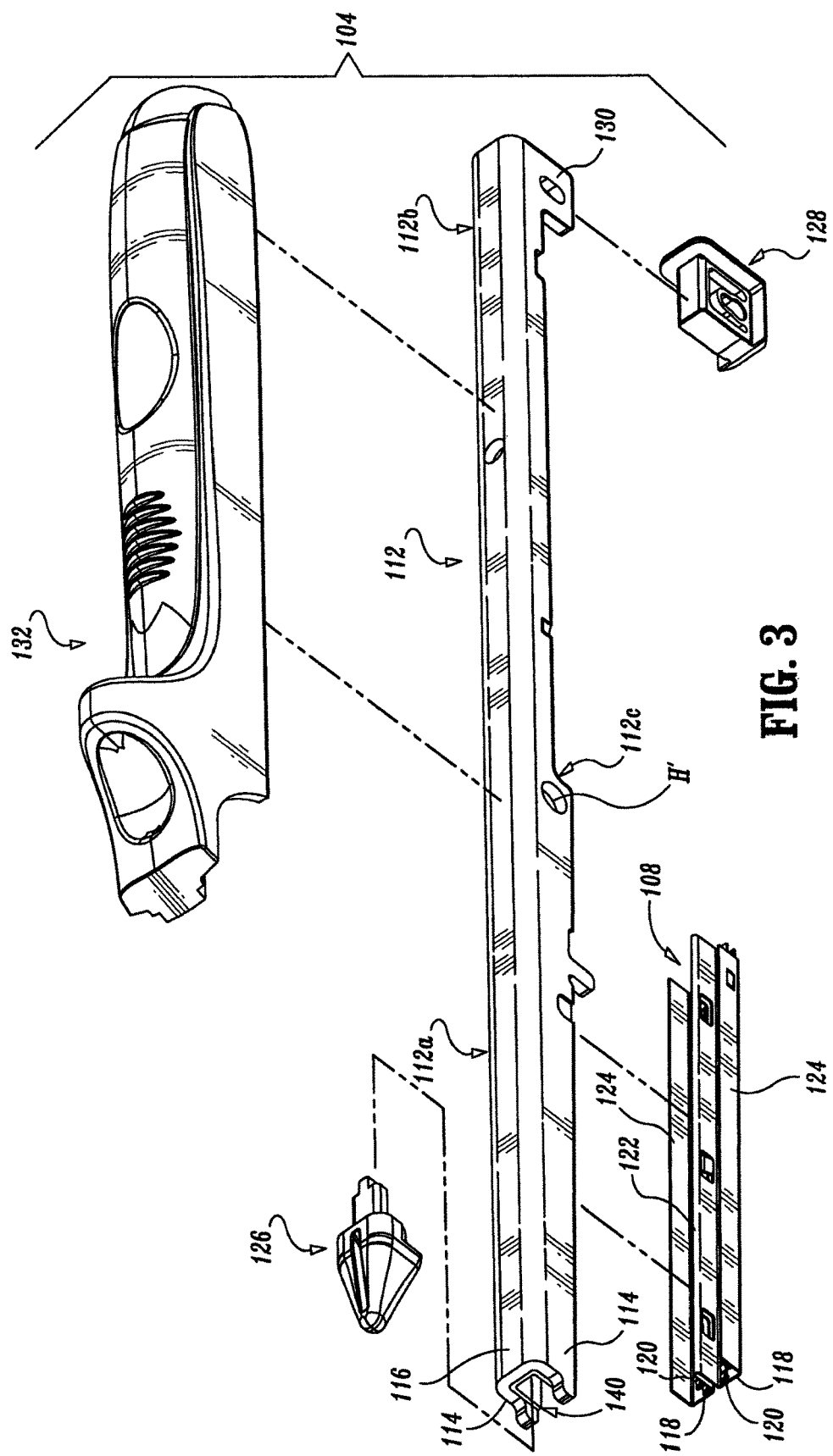
FIG. 3 is a top perspective view, with parts separated, of an anvil half-section of the surgical fastener applying apparatus of FIG. 1.

As seen in FIG. 3, anvil half-section 104 includes an anvil half-section channel member 112 having a distal end 112a, a proximal end 112b and a transition or intermediate point 112c. Channel member 112 has a substantially U-shaped transverse cross-sectional profile defined by a pair of substantially parallel juxtaposed side walls 114 interconnected by a base wall 116.

Anvil plate 108 is preferably configured and dimensioned to fit over side walls 114 of distal end 112a of channel member 112. As seen in FIG. 3, anvil plate 108 includes a pair of tissue contacting surfaces 118 each having a plurality of staple forming pockets 120 (i.e., anvil pockets, anvil depressions, etc.) formed therein. Preferably, anvil plate 108 includes a knife track 122 extending longitudinally between the pair of tissue contacting surfaces 118. Preferably, knife track 122 interconnects and separates the pair of tissue contacting surfaces 118 from one another. Anvil plate 108 further includes a pair of substantially parallel juxtaposed upstanding side walls 124 extending, one each, from a lateral side edge of the pair of anvil surfaces 118.

Anvil half-section 104 further includes a distal end cap 126 adapted to be snap-fit onto or into the distal tip of channel member 112. Preferably, end cap 126 is tapered to facilitate insertion of the distal tip into the target surgical site. Anvil half-section 104 can also include an end cap 128 to be received between a pair of spaced apart juxtaposed flanges 130 (one shown) extending from proximal end 112b of channel member 112.

Anvil half-section 104 can further include a contoured hand grip 132 configured and adapted to be snap-fit over proximal end 112b of channel member 112. Hand grip 132 desirably provides an operator of surgical stapling apparatus 100 with improved control and an increased degree of manipulation.

Figure 4:
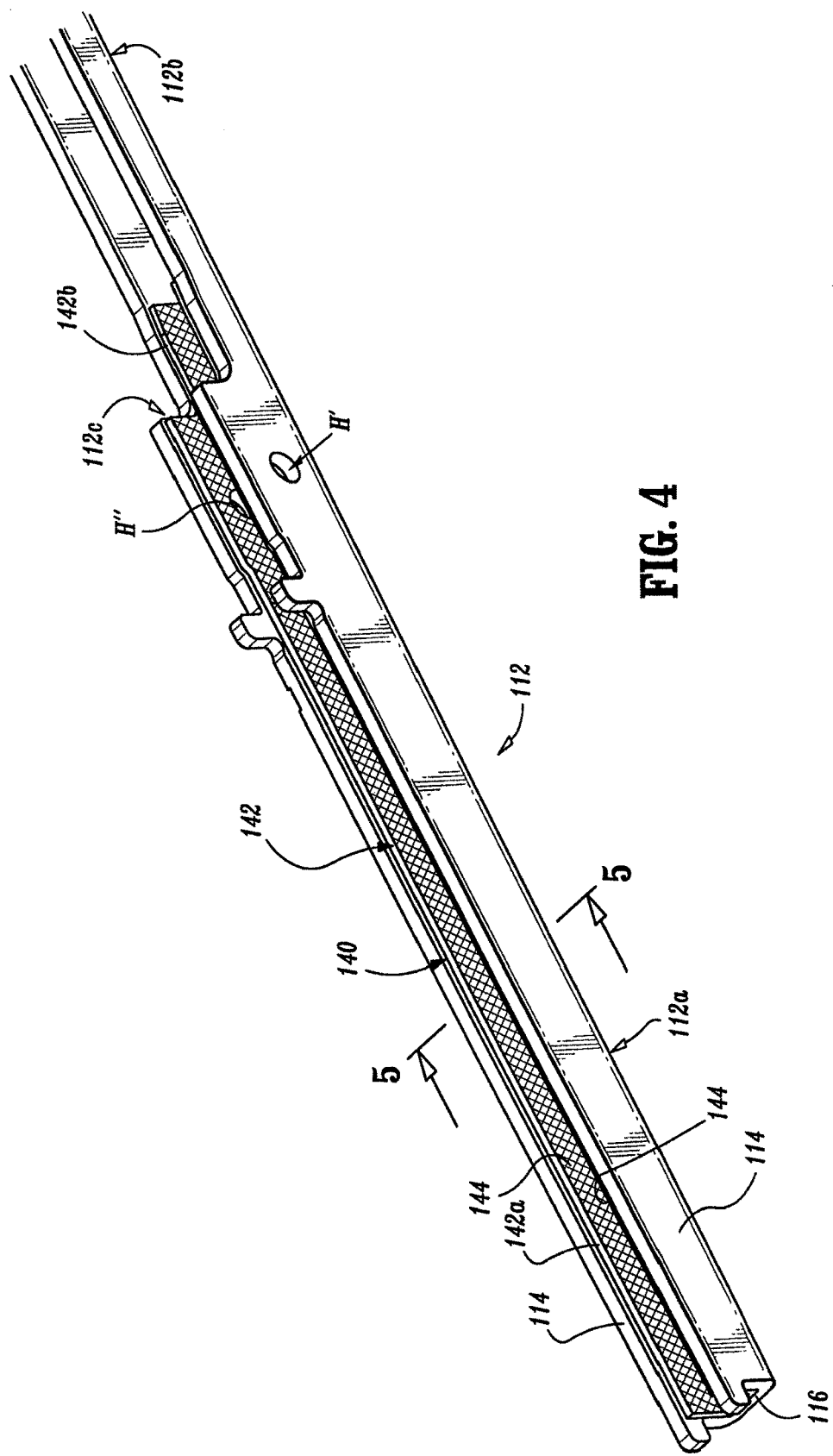
FIG. 4 is a bottom perspective view of an anvil half-section channel member of the anvil half-section of FIG. 3.
Figure 5:
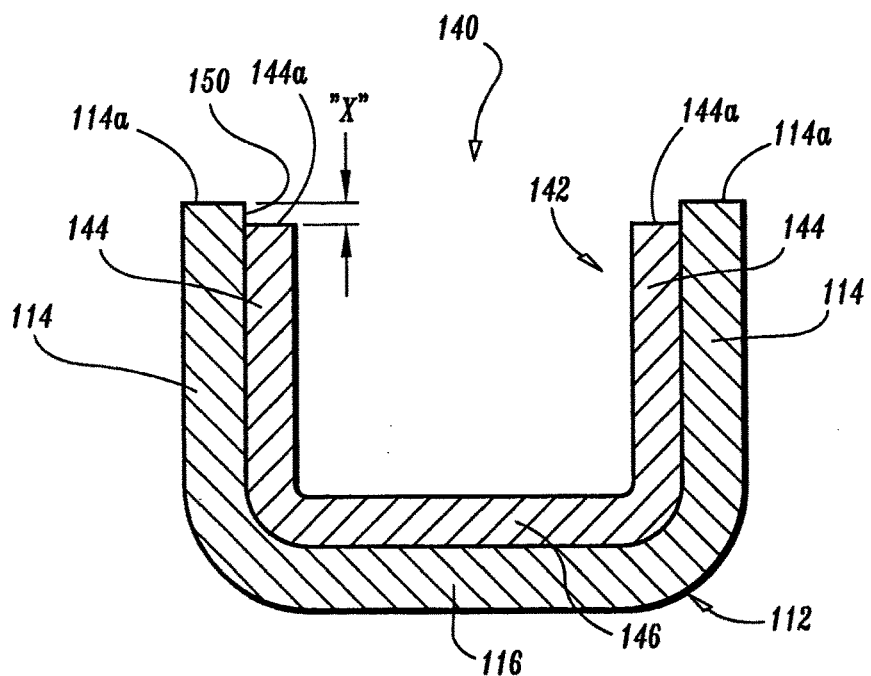
FIG. 5 is a transverse cross-sectional view of a portion of the distal end of the channel member of FIG. 4, as taken along section line 5-5 of FIG. 4.

As seen in FIGS. 3-5, anvil half-section 104 includes a deflection control system, generally designated 140 for reducing the rate of deflection of distal end 112a of channel member 112 as the force in direction "Y" increases and as the deflection distance of distal end 112a of channel member 112 increases. In this embodiment, deflection control system 140 includes a substantially U-shaped channel section 142 disposed between side walls 114 of channel member 112. As best seen in FIG. 5, channel section 142 is defined by a pair of parallel spaced apart juxtaposed side walls 144 interconnected by a base wall 146. In particular, side walls 144 of channel section 142 preferably have a height which is less than a height of side walls 114 of channel member 112 thus defining a reveal 150 having a height "X".

Height "X" of reveal 150 can be uniform or vary along the entire length of distal end 112a of channel member 112 and distal end 142a of channel section 142. Although, height "X" can taper in either a distal or a proximal direction, preferably it tapers in a distal direction, e.g., from being narrow or zero near the distal tip to a greater height near transition point 112c. Reveal 150 can have discrete regions or lengths, each of which, has a different height "X". Preferably, height "X" is from about 0.004 inches to about 0.10 inches, more preferably from about 0.004 inches to about 0.006 inches. As will be described in greater detail below, when height "X" is about 0.004 inches to about 0.006 inches, distal end 104a of anvil half-section 104 becomes stiffer sooner as compared to when height "X" is greater than 0.006 inches.

Channel section 142 extends from distal end 112a of channel member 112 to a portion of proximal end 112b. Channel section 142 is fixedly secured to channel member 112 preferably at least in a region proximal of but adjacent intermediate point 112c to allow channel section 142 to be free to float within channel member 112 in a region distal of intermediate point 112c (i.e., distal end 112a).

It is envisioned that channel section 142 can be secured at such locations to channel member 112 at suitable specific predetermined locations along the length thereof. In particular, side walls 144 of channel section 142 can be secured to corresponding side walls 114 of channel member 112, and base wall 146 of channel section 142 can be secured to base wall 116 of channel member 112.

Channel section 142 is preferably secured to channel member 112 by pinning (i.e., by extending a pin through channel section 142 and into an adjacent element or structure of apparatus 100), however, it is envisioned that channel section 142 can be secured to channel member 112 via any number of known techniques, such as, for example, welding, soldering, gluing, peening and the like. Most preferably, channel section 142 is, as will be explained, welded to channel member 112 and a cam 400 can extend through side walls 144 of channel section 142 to pin channel section 142 to side walls 144.

Channel section 142 is made from a rigid material which is resistant to bending, such as, for example, steel. While steel is preferred, it is contemplated that channel section 142 can be fabricated from other materials, such as, for example, titanium, polycarbonate, fiberglass, resins and the like, or any combination thereof.

It is further contemplated that each side wall 144 of channel section 142 have a pre-selected thickness. A relatively smaller thickness provides less rigidity while a relatively larger thickness provides increased rigidity. It is still further contemplated that each side wall 144 can have a uniform or varying thickness along its length.

In operation, channel section 142 increases the rigidity of channel member 112 (i.e., reduces the rate of deflection) after channel member 112 has undergone a predetermined amount of deflection in direction "Y" (e.g., transverse to a longitudinal axis of apparatus 100 and substantially normal to the plane of the tissue contacting surface of anvil 108) thereby reducing the rate of deflection of distal end 112a of channel member 112. As will be used herein, the recitation "tissue having a relatively smaller thickness" is understood to mean tissue having a thickness which will not tend to cause distal end 104a of anvil half-section 104 to deflect an amount sufficient to result in the operation of deflection control system 140. Also, the recitation "tissue having a relatively larger thickness" is understood to mean tissue having a thickness which will tend to cause distal end 104a of anvil half-section 104 to deflect an amount sufficient to result in the operation of deflection control system 140.

Surgical stapling apparatus 100 preferably is initially set-up such that tissue gap "G" has a slight taper from a proximal end to a distal end (i.e., tissue gap "G" reduces in height from the proximal end to the distal end). In this manner, when tissue having a relatively smaller thickness is clamped between the distal ends 104a, 102a of anvil half-section 104 and cartridge receiving half-section 102, the distal ends 104a, 102a of anvil half-section 104 and/or cartridge receiving half-section 102 will deflect an amount sufficient to cause tissue gap "G" to have a substantially uniform dimension from proximal end to distal end. As such, the staples which are fired from staple cartridge assembly 106 are substantially uniformly formed from the proximal end of staple cartridge assembly 106 to the distal end of staple cartridge assembly 106.

When tissue having a relatively larger thickness is clamped between distal ends 104a, 102a of anvil half-section 104 and cartridge receiving half-section 102, channel section 142 of deflection control system 140 causes distal end 104a of anvil half-section 104 to undergo a two-stage deflection. In the first stage of deflection the deflection force acts solely on edge surfaces 114a of side walls 114, oriented in the direction of the tissue to be clamped, of channel member 112 resulting in distal end 104a of anvil half-section 104 undergoing an initial rate of deflection in direction "Y", until height "X" of reveal 150, between side walls 144 of channel section 142 and side walls 114 of channel member 112, is reduced to zero (i.e., the height of side walls 144 of channel section 142 are even with the height of side walls 114 of channel member 112).

When tissue having a relatively larger thickness is clamped between distal ends 104a, 102a of anvil half-section 104 and cartridge receiving half-section 102, channel section 142 of deflection control system 140 causes distal end 104a of anvil half-section 104 to undergo a two-stage deflection. In the first stage of deflection the deflection force acts solely on edge surfaces 114a of side walls 114, oriented in the direction of the tissue to be clamped, of channel member 112 resulting in distal end 104a of anvil half-section 104 undergoing an initial rate of deflection in direction "Y", until height "X" of reveal 150, between side walls 144 of channel section 142 and side walls 114 of channel member 112, is reduced to zero (i.e., the height of side walls 144 of channel section 142 are even with the height of side walls 114 of channel member 112).

In addition, during the first stage of deflection, the height of tissue gap "G" is urged from its initial tapered configuration to a second configuration which is less tapered (i.e., less angled). At this point, edge surfaces 144a of side walls 144 of channel section 142 and edge surfaces 114a of side walls 114 of channel member 112 are in contact with the underside of tissue contacting surfaces 118 of anvil plate 108 thereby making distal end 104a of anvil half-section 104 stiffer and/or more rigid thus reducing the tendency of distal end 104a of anvil half-section 104 to deflect.

Once height "X" of reveal 150 reaches zero, each edge surface 114a, 144a of side walls 114 and 144, respectively, is in contact with the underside of tissue contacting surfaces 118 of anvil plate 108 and distal end 104a of anvil half-section 104 and undergoes a second stage of deflection. In other words, the deflecting force now acts on side walls 114 and 144 in order to urge and deflect distal end 104a of anvil half-section 104. Since the deflecting force must now act on both side walls 114 and 144, distal end 104a of anvil half-section 104 is effectively reinforced and stiffened from this time forward.

In the second stage, deflection control system 140 causes distal end 104a of anvil half-section 104 to undergo a rate of deflection which is less than the initial rate of deflection. In addition, during the second stage of deflection, the height of tissue gap "G" is urged from its tapered configuration to a configuration that is less tapered or has a substantially uniform dimension (i.e., uniform height) from the distal end to the proximal end. Deflection control system 140 in effect prevents the distal end of tissue gap "G" from having a reverse tapered configuration (i.e., the distal end having a larger height than the proximal end).

Figure 6:
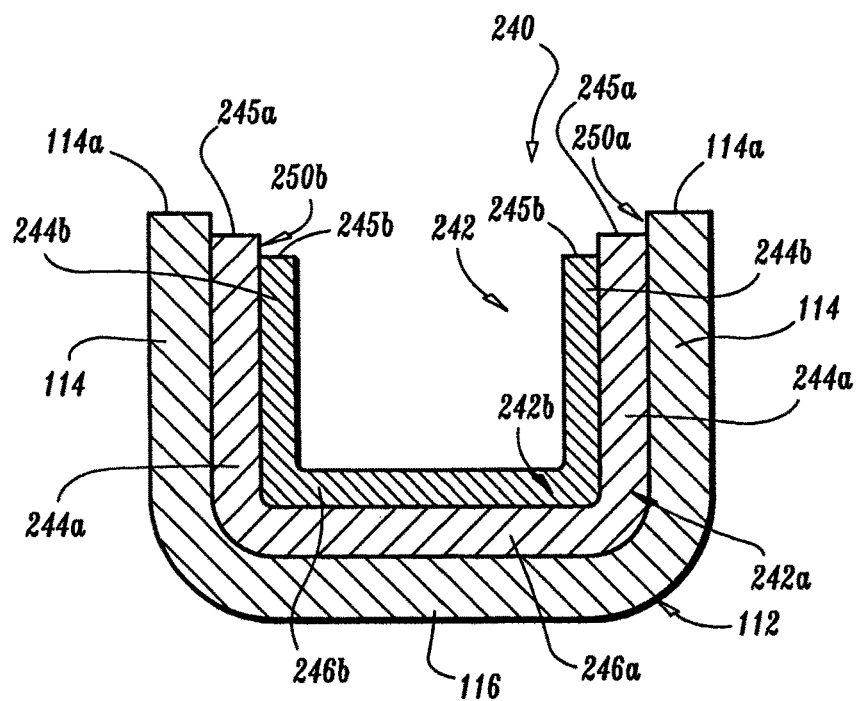
FIG. 6 is a transverse cross-sectional view of a portion of the distal end of a channel member, in accordance with an alternative embodiment of the present disclosure, as would be seen along section line 5-5 of FIG. 4.

Turning now to FIG. 6, a deflection control system, for controlling and/or incrementally reducing the rate of deflection of distal end 112a of channel member 112, in accordance with an alternative embodiment of the present disclosure, is shown generally as 240. Deflection control system 240 is a dual layered substantially U-shaped channel section 242 configured and dimensioned to be disposed in and between side walls 114 of channel member 112. Channel section 242 includes an outer channel section 242a and an inner channel section 242b. Outer channel section 242a is defined by a pair of parallel spaced apart juxtaposed side walls 244a interconnected by a base wall 246a. In particular, side walls 244a of channel section 242a preferably have a height which is less than a height of side walls 114 of channel member 112 thus defining a first reveal 250a.

Inner channel section 242b is defined by a pair of parallel spaced apart juxtaposed side walls 244b interconnected by a base wall 246b. In particular, side walls 244b of channel section 242b preferably have a height which is less than a height of side walls 244a of channel section 242a thus defining a second reveal 250b. Preferably, inner channel section 242b is pinned by a cam member (not shown) near intersecting point 112c, secured to outer channel section 242a at a region proximal of intermediate point 112c and is secured at a region near the distal tip (see FIG. 4). Inner channel section 242b is likewise preferably secured to outer channel section 242a via pinning or in any manner as described above with regard to channel section 142 of FIGS. 3-5.

When tissue having a relatively smaller thickness is clamped between distal ends 104a, 102a of anvil half-section 104 and cartridge receiving half-section 102 deflection control system 240 functions basically the same manner as deflection control system 140. When tissue having a relatively larger thickness is clamped between distal ends 104a, 102a of anvil half-section 104 and cartridge receiving half-section 102, channel section 242 of deflection control system 240 causes distal end 104a of anvil half-section 104 to undergo a three-stage deflection. In the first stage of deflection the deflection force acts solely on edge surfaces 114a of side walls 114 of channel member 112 resulting in distal end 104a of anvil half-section 104 undergoing an initial rate of deflection in direction "Y" until height "X" of reveal 250a, between side walls 244a of outer channel section 242a and side walls 114 of channel member 112 is reduced to zero (i.e., the height of side walls 244a of outer channel section 242a are even with the height of side walls 114 of channel member 112). At this point, edge surfaces 114a and 245a of respective side walls 114 and 244a are each in contact with the underside of tissue contacting surfaces 118 of anvil plate 108 thereby making distal end 104a of anvil half-section 104 stiffer and/or more rigid thus reducing its tendency to deflect.

Once reveal 250a reaches zero, each edge surface 114a, 245a of side walls 114 and 244a, respectively, is in contact with the underside of tissue contacting surfaces 118 of anvil plate 108 and distal end 104a of anvil half-section 104 undergoes a second stage of deflection. Since the deflecting force must now act on side walls 114 and 244a, distal end 104a of anvil half-section 104 is effectively reinforced and stiffened from this time forward. In the second stage, channel section 242 of deflection control system 240 causes distal end 104a of anvil half-section 104 to undergo a second degree of deflection which is less than the initial degree of deflection at a second rate of deflection which is less than the initial rate of deflection.

During the second stage of deflection, distal end 104a of anvil half-section 104 and outer channel section 242a deflect, in direction "Y", until reveal 250b between side walls 244b of inner channel section 242b and side walls 244a of outer channel section 242a is reduced to zero. At this point, edge surfaces 114a, 245a and 245b of respective side walls 114, 244a and 244b are in contact with the underside of tissue contacting surfaces 118 of anvil plate 108 thereby making distal end 104a of anvil half-section 104 still more stiffer and/or still more rigid thus further reducing the tendency of distal end 104a of anvil half-section 104 to deflect.

Once reveal 250b reaches zero, each edge surface 114a, 245a and 245b of side walls 114, 244a and 244b, respectively, is in contact with the underside of tissue contacting surfaces 118 of anvil plate 108 and distal end 104a of anvil half-section 104 undergoes a third stage of deflection. Since the deflecting force must now act on side walls 114, 244a and 244b, distal end 104a of anvil half-section 104 is effectively further reinforced and stiffened from this time forward.

Channel sections 242a and 242b are each preferably made from a rigid material, such as for example, steel. While steel is preferred, it is contemplated that each of channel section 242a and 242b can each be fabricated from other materials, such as, for example, titanium, polycarbonate, fiber glass, resins and the like or any combination thereof.

Side walls 244a of outer channel section 242a and side walls 244b of inner channel section 242b each preferably have a uniform height along their respective lengths. However, it is contemplated that side walls 244a of outer channel section 242a and side walls 244b of inner channel section 242b can have varying heights along their lengths. Preferably, side walls 244a of outer channel section 242a and side walls 244b of inner channel section 242b each have a uniform thickness, however, it is envisioned that they can have varying thicknesses along their lengths. The height and thickness of each side wall 244a of outer channel section 242a and of each side wall 244b of inner channel section 242b is specifically selected depending on the degree of stiffness desired and on which regions of anvil half-section 104 are desired to be stiffened.

Turning now to FIGS. 7-10, a deflection control system, for controlling and/or reducing the rate of deflection of distal end 112a of channel member 112, in accordance with a preferred embodiment of the present disclosure is shown generally as 340. Deflection control system 340 includes a pair of parallel spaced apart juxtaposed reinforcing plates and/or ribs 344, each one to be secured to a respective side wall 114 of channel member 112.

Each reinforcing rib 344 is preferably secured to a respective side wall 114 of channel member 112 at a region proximal of intermediate point 112c (See FIG. 4). Preferably, each reinforcing rib 344 is secured to its respective side wall 114 by being welded or pinned at a location proximal of intermediate point 112c. Other methods of securing reinforcing ribs 344 to side walls 114 are contemplated, such as, for example, gluing, adhering, peening and the like. Each reinforcing rib 344 is preferably made from stainless steel and has a uniform height and thickness. In particular, reinforcing ribs 344 preferably have a height which is less than a height of side walls 114 of channel member 112 thus defining a reveal 350.

Figure 9:
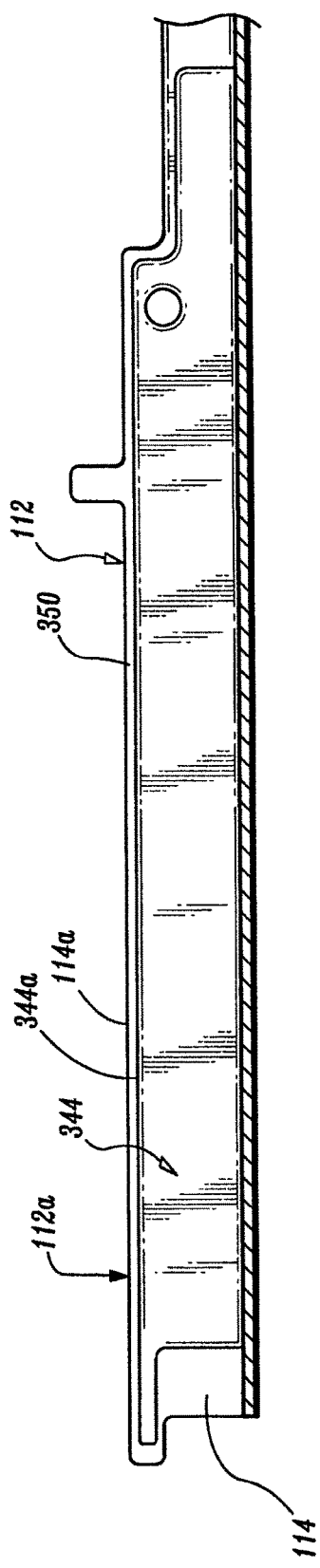
FIG. 9 is a longitudinal cross-sectional view of a portion of the distal end of the channel member of FIGS. 7 and 8 when no load is applied to a distal end thereof.
Figure 10:
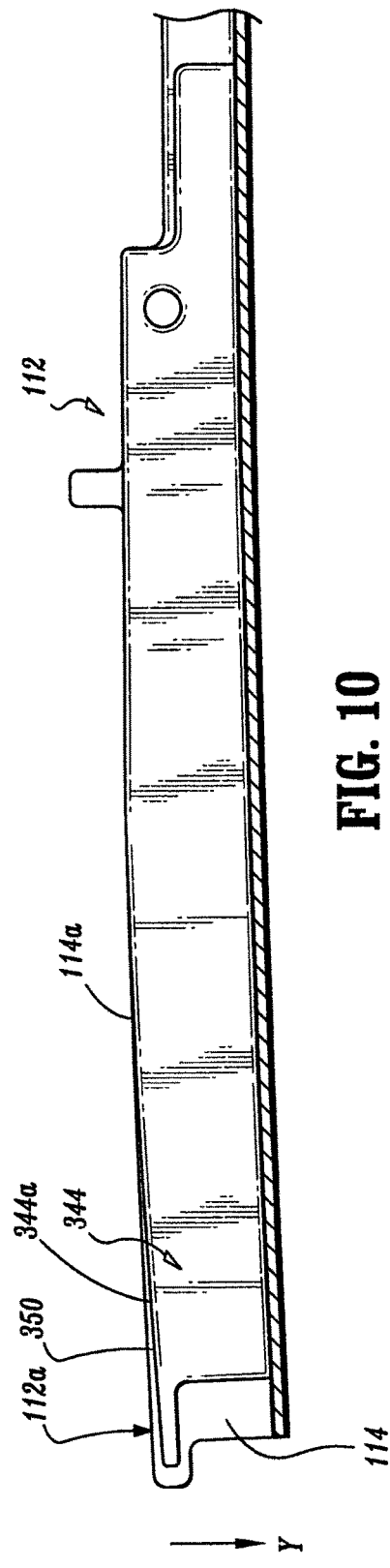
FIG. 10 is a longitudinal cross-sectional view of a portion of the distal end of the channel member of FIG. 9 having a load applied to a distal end thereof.

When tissue having a relatively smaller thickness is clamped between distal ends 104a, 102a of anvil half-section 104 and cartridge receiving half-section 102, deflection control system 340 functions in the same manner as described above for control system 140. As seen in FIGS. 9 and 10, when tissue having a relatively larger thickness is clamped between distal ends 104a, 102a of anvil half-section 104 and cartridge receiving half-section 102, reinforcing ribs 344 of deflection control system 340 causes distal end 104a of anvil half-section 104 to undergo a two-stage deflection. In the first stage of deflection the deflection force acts solely on edge surfaces 114a of side walls 114 of channel member 112 resulting in distal end 104a of anvil half-section 104 undergoing an initial rate of deflection in direction "Y" until reveal 350 between reinforcing ribs 344 and side walls 114 of channel member 112 is reduced to zero (i.e., the height or edges of reinforcing ribs 344 are even with the height or edges of side walls 114 of channel section 112).

During the first stage of deflection, the height of tissue gap "G" is urged from its initial tapered configuration to a second configuration which is less tapered (i.e., less angled) than the initial tapered configuration or substantially uniform. At this point, edge surfaces 114a of side walls 114 and edge surfaces 344a of reinforcing rib 344 are in contact with the underside of tissue contacting surfaces 118 of anvil plate 108 thereby making distal end 104a of anvil half-section 104 stiffer and/or more rigid thus reducing the tendency of distal end 104a of anvil half-section 104 to deflect. Once reveal 350 reaches zero, each edge surface 114a, 344a of side walls 114 and of reinforcing rib 344, respectively, are in contact with the underside of tissue contacting surfaces 118 of anvil plate 108 and distal end 104a of anvil half-section 104 undergoes a second stage of deflection.

In the second stage, deflection control system 340 causes distal end 104a of the anvil half-section 104 to undergo a rate of deflection which is less than the initial rate of deflection. In addition, during the second stage of deflection the height of tissue gap "G" is urged from its second less tapered configuration to a configuration having a substantially uniform dimension (i.e., uniform height) from the distal end to the proximal end. Deflection control system 340 in effect prevents the distal end of tissue gap "G" from having a reverse tapered configuration (i.e., the distal end having a larger height than the proximal end).

Turning now to FIGS. 11-13, a deflection control system, for controlling and/or incrementally reducing the rate of deflection of distal end 112a of channel member 112, in accordance with yet another embodiment of the present disclosure is shown generally as 460 (see FIG. 12). Deflection control system 460 is generally in the form of a leaf-spring and includes a layered reinforcing member 462 (see FIG. 12) having a plurality of individual reinforcing plates (e.g., 462a, 462b and 462c) extending longitudinally between side walls 114 of channel member 112 and resting atop base wall 116. While deflection control system 460 is shown as having three reinforcing members, it is envisioned that deflection control system 460 can have any number of reinforcing members, including, and not limited to, one, two, four, etc.

Deflection control system 460 further includes a pin member 468 extending through a series of elongate slots 470 formed in reinforcing member 462. Preferably, a proximal end 464 of reinforcing member 462 is fixedly secured to channel member 112, by means of welding, riveting and the like, at a location proximal of intermediate portion 112c while a distal end 466 of reinforcing member 462 is preferably slidably secured to distal end 112a by pin member 468. Distal end 466 of reinforcing member 462 is preferably pinned at a location proximate to the distal-most edge 112d of channel member 112. Pin member 468 includes a body portion 472 having a first end 474 fixedly secured to base wall 116 of channel member 112 and a second end 476 extending through reinforcing member 462, and an enlarged head 478 secured to second end 476. Head 478 is configured and dimensioned to be larger than elongate slots 470 and to rest on the upper-most reinforcing plate. Body portion 472 of pin member 468 is dimensioned such that head 478 maintains reinforcing plates 462a-462c in sliding contact with one another. While it is preferred that pin member 468 extend through base wall 116 of channel member 112 it is envisioned that pin member 468 can extend through side walls 114 of channel member 112 at a location to engage reinforcing member 462.

Reinforcing member 462 includes a first reinforcing plate 462a having a first elongate slot 470a formed therein and extending in a longitudinal direction, wherein first elongate slot 470a has a first length. Reinforcing member 462 further includes a second reinforcing plate 462b having a second elongate slot 470b formed therein and extending in a longitudinal direction, wherein second elongate slot 470b has a second length which is greater than the first length of first elongate slot 470a. Reinforcing member 462 further includes a third reinforcing plate 462c having a third elongate slot 470c formed therein and extending in a longitudinal direction, wherein third elongate slot 470c has a third length which is greater than the second length of second elongate slot 470b.

In operation, reinforcing member 462 increases the rigidity of channel member 112 only after channel member 112 has undergone a predetermined amount of deflection in direction "Y", to thereby reduce the rate of deflection of distal end 112a of channel member 112. Accordingly, when tissue having a relatively small thickness is clamped between distal ends 104a, 102a of anvil half-section 104 and cartridge receiving half-section, distal end 104a of anvil half-section 104 will tend to deflect an amount sufficient for tissue gap "G" to have a substantially uniform dimension from the proximal end to the distal end thereof.

When tissue having a relatively larger thickness is clamped between distal ends 104a, 102a of anvil half-section 104 and cartridge receiving half-section 102, deflection control system 460 causes distal end 104a of anvil half-section 104 to undergo a four-stage deflection. In a first stage of deflection, distal end 112a of channel member 112 undergoes an initial rate of deflection, in direction "Y", until the distal surface of first slot 470a of first reinforcement plate 462a contacts pin member 468 thus beginning a second stage of deflection.

In the second stage of deflection, distal end 112a of channel member 112 and first reinforcement plate 462a undergo a second rate of deflection, in direction "Y", until the distal surface of second slot 470b of second reinforcement plate 462b contacts pin member 468, thus beginning a third stage of deflection. Since the deflection force is now acting on distal end 112a of channel member 112 of anvil half-section 104 and on first reinforcement plate 462a, the second rate of deflection is less than the first rate of deflection.

In the third stage of deflection, distal end 112a of channel member 112 and both first and second reinforcement plates 462a and 462b undergo a third rate of deflection, in direction "Y", until the distal surface of third slot 470c of third reinforcement plate 462c contacts pin member 468, thus beginning a fourth stage of deflection. Since the deflection force is now acting on distal end 112a of channel member 112 and both first and second reinforcement plates 462a and 462b, the third rate of deflection is less than the second rate of deflection.

In the fourth stage of deflection, distal end 112a of channel member 112 and each of first, second and third reinforcement plates 462a-462c undergo a fourth rate of deflection, in direction "Y". Since the deflection force is now acting on distal end 112a of channel member 112 and on each of first, second and third reinforcement plates 462a-462c, the fourth rate of deflection is less than the third rate of deflection.

At each stage of deflection, distal end 112a of channel member 112 is further stiffened by the interaction of deflection control system 460 with distal end 112a of channel member 112. Deflection control system 460 will permit distal end 112a to deflect an initial amount, in direction "Y", in a manner similar to if deflection control system 460 was not provided. However, when the deflection, in direction "Y", becomes greater than a predetermined amount, deflection control system 460 is engaged and distal end 112a of channel member 112 is stiffened. As described above, deflection control system 460 can provide distal end 112a of channel member 112 with multiple stages of incremental stiffening, however, it is within the scope of the present disclosure that deflection control system 460 provides distal end 112a of channel member 112 with a single stage of stiffening.

Turning now to FIGS. 14-16, a deflection control system, for controlling and/or incrementally reducing the rate of deflection of distal end 112a of channel member 112, in accordance with still another embodiment of the present disclosure is shown generally as 560. Deflection control system 560 is generally in the form of a leaf-spring and includes a layered reinforcing member 562 having a plurality of individual reinforcing plates (e.g., 562a, 562b and 562c) extending longitudinally between side walls 114 of channel member 112 and resting atop base wall 116.

Deflection control system 560 further includes a pair of juxtaposed shoulders 580 preferably integrally formed with and extending transversely from an inner surface of side walls 114 of channel member 112. While a pair of integral shoulders 580 are shown, it is contemplated that shoulders 580 can be formed from elements (i.e., bolts, screws, pins, brackets, etc.) extending through side walls 114. Each shoulder 580 includes a body portion 582 having a height greater than reinforcing member 562 and a head portion 584 configured and dimensioned to overlie reinforcing member 562.

Body portion 582 of shoulders 580 preferably extends into a series of elongate recesses 590 formed along the lateral sides of reinforcing member 562. Preferably, a proximal end of 564 reinforcing member 562 is fixedly secured to channel member 112, by means of welding, riveting and the like, at a location proximal of intermediate portion 112c while a distal end of reinforcing member 562 is preferably slidably coupled to distal end 112a via shoulders 580.

Reinforcing member 562 includes a first reinforcing plate 562a having a first pair of elongate recesses 590a formed along each lateral side thereof and extending in a longitudinal direction, wherein the first pair of elongate recesses 590a has a first length. Reinforcing member 562 further includes a second reinforcing plate 562b having a second pair of elongate recesses 590b formed in each lateral side thereof and extending in a longitudinal direction, wherein the second pair of elongate recesses 590b has a second length which is greater than the first length of first pair of elongate recesses 590a. Reinforcing member 562 further includes a third reinforcing plate 562c having a third pair of elongate recesses 590c formed in each lateral side thereof and extending in a longitudinal direction, wherein the third pair of elongate recesses 590c has a third length which is greater than the second length of the second pair of elongate recesses 590b.

In operation, reinforcing member 562 functions in the same manner as reinforcing member 562. In particular, reinforcing member 562 increases the rigidity of channel member 112 only after channel member 112 has undergone a predetermined amount of deflection in direction "Y". When tissue having a relatively larger thickness is clamped between distal ends 104a, 102a of anvil half-section 104 and cartridge receiving half-section 102, deflection control system 560 causes distal end 104a of anvil half-section 104 to undergo a four-stage deflection. In a first stage of deflection, distal end 112a of channel member 112 undergoes an initial rate of deflection, in direction "Y", until the distal surfaces of the first pair of recesses 590a of first reinforcement plate 562a contacts shoulders 580 thus beginning a second stage of deflection.

In the second stage of deflection, distal end 112a of channel member 112 and first reinforcement plate 562a undergo a second rate of deflection, in direction "Y", until the distal surfaces of the second pair of recesses 590b of second reinforcement plate 562b contacts shoulders 580, thus beginning a third stage of deflection. Since the deflection force is now acting on distal end 112a of channel member 112 of anvil half-section 104 and on first reinforcement plate 562a, the second rate of deflection is less than the first rate of deflection.

In the third stage of deflection, distal end 112a of channel member 112 and both first and second reinforcement plates 562a and 562b undergo a third rate of deflection, in direction "Y", until the distal surfaces of the third pair of recesses 590c of third reinforcement plate 562c contacts shoulders 580, thus beginning a fourth stage of deflection. Since the deflection force is now acting on distal end 112a of channel member 112 and both first and second reinforcement plates 562a and 562b, the third rate of deflection is less than the second rate of deflection.

In the fourth stage of deflection, distal end 112a of channel member 112 and each of first, second and third reinforcement plates 562a-562c undergo a fourth rate of deflection, in direction "Y". Since the deflection force is now acting on distal end 112a of channel member 112 and on each of first, second and third reinforcement plates 562a-562c, the fourth rate of deflection is less than third rate of deflection.

At each stage of deflection, distal end 112a of channel member 112 is further stiffened by the interaction of deflection control system 560 with distal end 112a of channel member 112. When the deflection, in direction "Y", becomes greater than a predetermined amount, deflection control system 560 is engaged and distal end 112a of channel member 112 is stiffened. As described above, deflection control system 560 can provide distal end 112a of channel member 112 with multiple stages of stiffening, however, it is within the scope of the present disclosure that deflection control system 560 provides distal end 112a of channel member 112 with a single stage of stiffening.

As seen in FIGS. 8-12, reinforcing plates 462a-462c and reinforcing plates 562a-562c (for the sake of simplicity, hereinafter referred to as "reinforcing plates 462a-462c") can each have a different thickness from a distal end to a proximal end thereof. In this manner, the degree of stiffening created by each reinforcing plate 462a-462c will be different. In other words, a relatively thicker reinforcing plate will result in a greater degree of stiffening while a relatively thinner reinforcing plate will result in a lesser degree of stiffening. While reinforcing plate 462a is shown as the thickest (i.e., providing the greatest degree of stiffening) and reinforcing plate 462c is shown as the thinnest (i.e., providing the least degree of stiffening), it is contemplated that the position of reinforcing plates 462a and 462c can be reversed. It is further contemplated that any combination of thicknesses and relative position of reinforcing plates 462a-462c can be provided to achieve a desired degree and rate of stiffening of distal end 112a of channel member 112.

Reinforcing plates 462a-462c are preferably each fabricated from stainless steel, however, it is contemplated that reinforcing plates can be fabricated from any material capable of increasing the rigidity of distal end 112a of channel member 112, such as, for example, titanium, polycarbonate, fiberglass, resins and the like or any combination thereof.

In each of the above-described deflection systems, it is desirable that the deflection system has a low profile or that the deflection system is situated to the lateral sides of channel member 112. In this manner, deflection systems will not result in the alteration of the depth of knife track 122 and/or the operation of the knife blade (not shown) reciprocatingly disposed within knife track 122.

Figure 17:
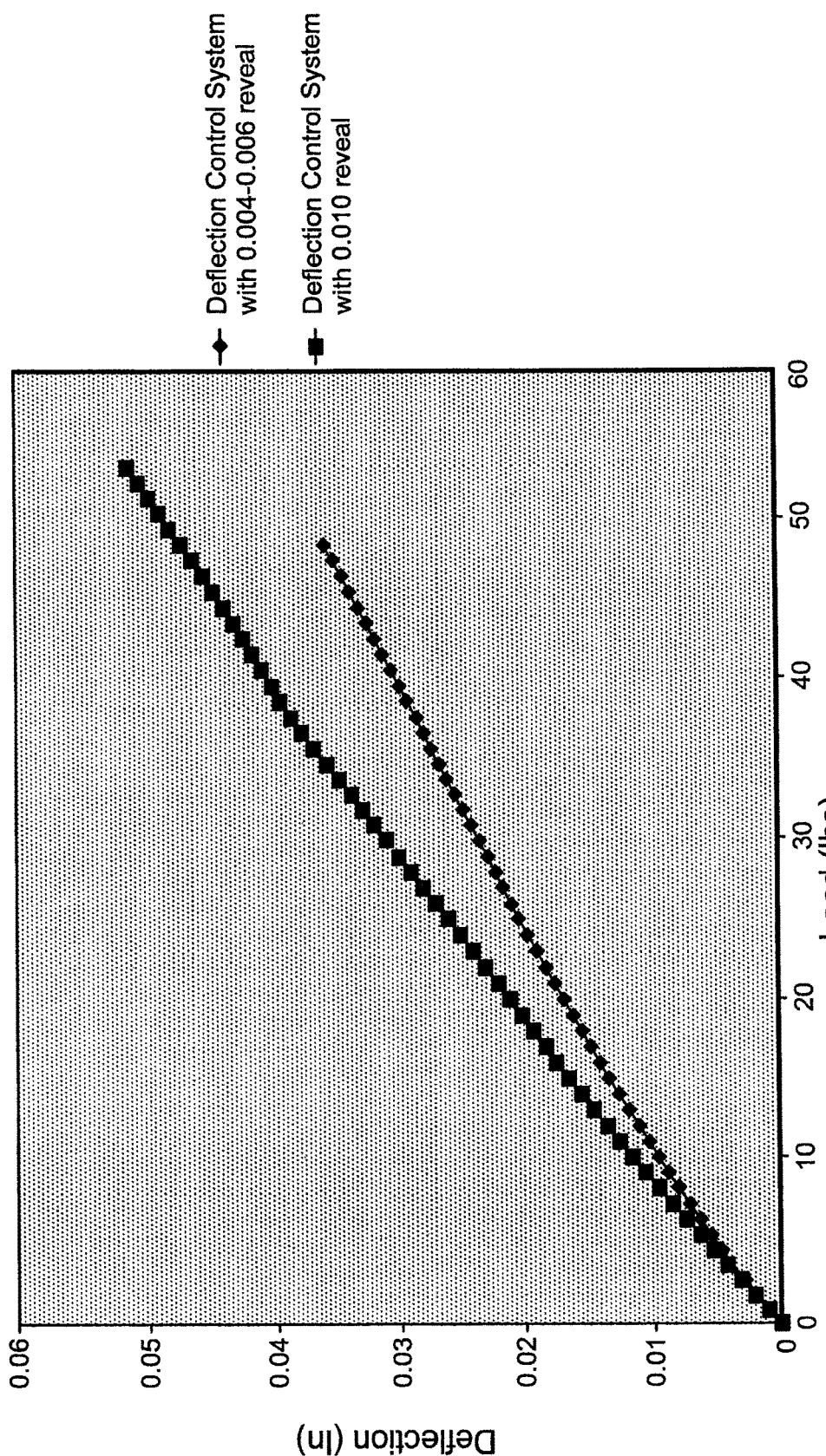
FIG. 17 is a graph illustrating the effects of the use of a deflection control system, in accordance with the present disclosure, in an anvil half-section.

FIG. 17 is a graph illustrating the effects of use of any of the deflection control systems disclosed herein. As seen in FIG. 17, for deflection control systems having a reveal of about 0.004 to about 0.006 inches a change in the rate of deflection, as evidenced by a change in the slope of the corresponding plot, is experienced at approximately 15 lbs. Also as seen in FIG. 17, for deflection control systems having a reveal of about 0.010 inches a change in the rate of deflection, as evidenced by a change in the slope of the corresponding plot, is experienced at approximately 34 lbs.

Turning now to FIGS. 18-23, a deflection control system, for controlling and/or reducing the rate of deflection of distal end 112a of channel member 112, in accordance with the preferred embodiment of the present disclosure, is shown generally as 640. Deflection control system 640 includes a pair of parallel spaced apart juxtaposed reinforcing plates and/or ribs 344, each one secured to a respective side wall 114 of channel member 112.

Figure 18:
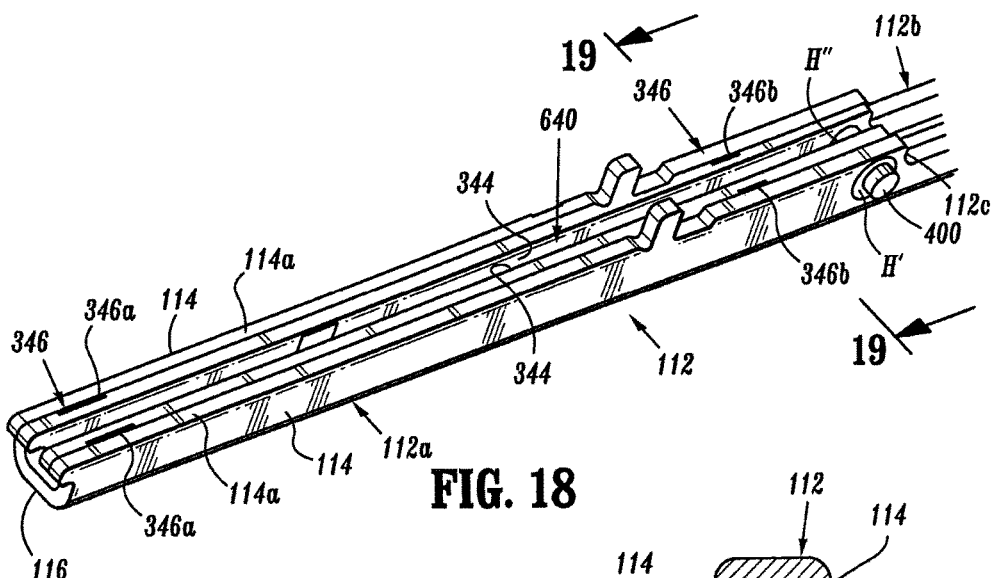
FIG. 18 is a bottom perspective view of a portion of the distal end of a channel member of an anvil half-section, in accordance with another embodiment of the present disclosure.
Figure 19:
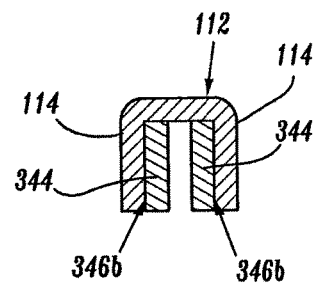
FIG. 19 is a transverse cross-sectional view of the channel member of FIG. 18, as would be seen along line 19-19 of FIG. 18.
Figure 20:
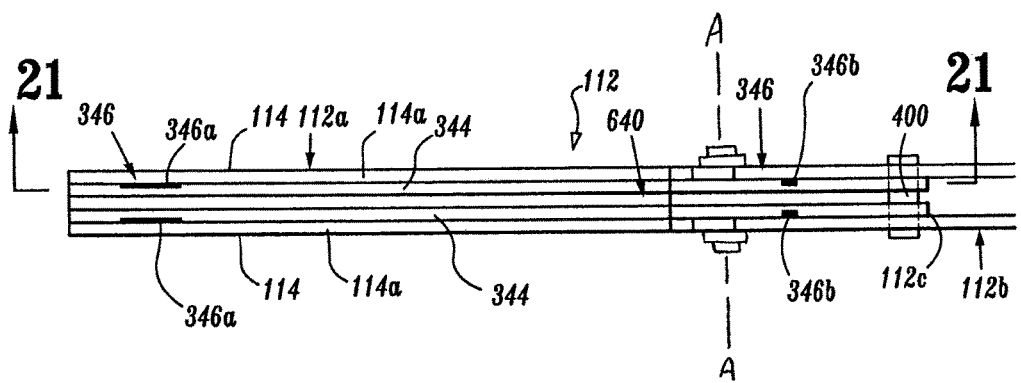
FIG. 20 is a bottom plan view of the distal end of the channel member of FIG. 18.

Preferably, each reinforcing rib 344 is secured to side walls 114 of channel member 112 by welds 346. At least one weld 346, preferably a pair of welds 346a, 346b can be used to secure each reinforcing rib 344 to side wall 114. As seen in FIGS. 18-20, welds 346a are provided near distal tip 112d of channel member 112 and welds 346b are provided near intermediate point 112c of channel member 112. Preferably, welds 346b are provided proximal of intermediate point 112c of channel member 112 and of cam member 400 of anvil half-section 104. (see FIGS. 2, 18 and 20)

Figure 21:
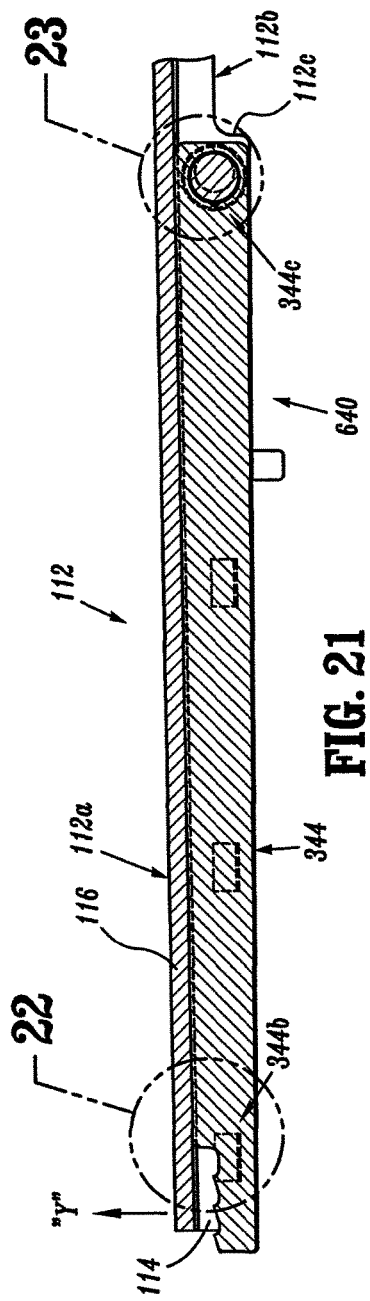
FIG. 21 is a longitudinal cross-sectional view of a portion of the distal end of the channel member of FIGS. 18 and 19, as would be seen along section line 21-21 of FIG. 20.
Figure 23:
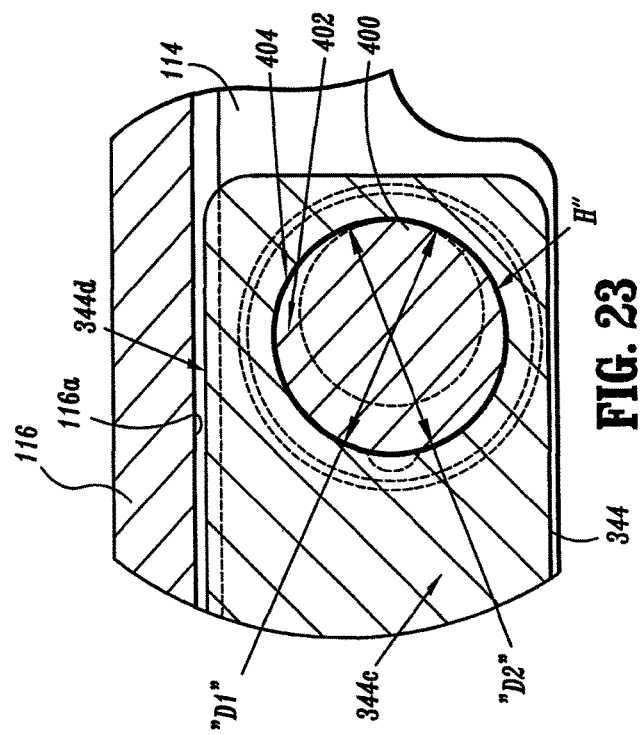
FIG. 23 is an enlarged view of the area indicated 23 of FIG. 21.
Figure 22:
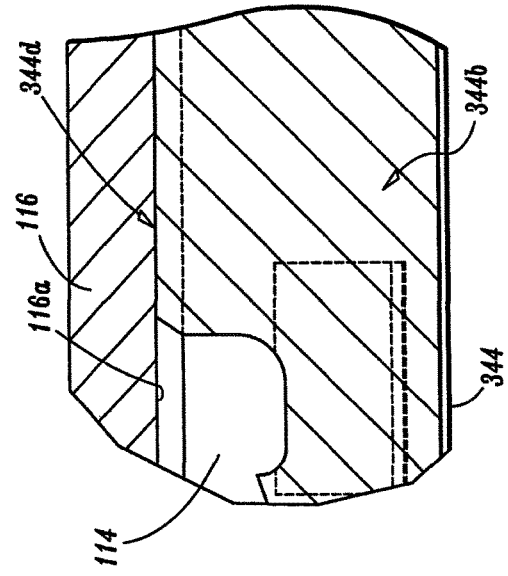
FIG. 22 is an enlarged view of the area indicated 22 of FIG. 21.

Preferably, each reinforcing rib 344 is welded to a respective side wall 114 such that an upper surface 344d of reinforcing rib 344 contacts or substantially contacts an inner surface 116a of base wall 116. As seen in FIGS. 21 and 22, a distal end 344b of reinforcing rib 344 is welded to side wall 114 such that upper surface 344d of reinforcing rib 344 is in contact with inner surface 116a of base wall 116. As seen in FIGS. 21 and 23, a proximal end 344c of reinforcing rib 344 is welded to side wall 114 such that upper surface 344d of reinforcing rib 344 is spaced a distance from inner surface 116a of base wall 116.

Figure 7:
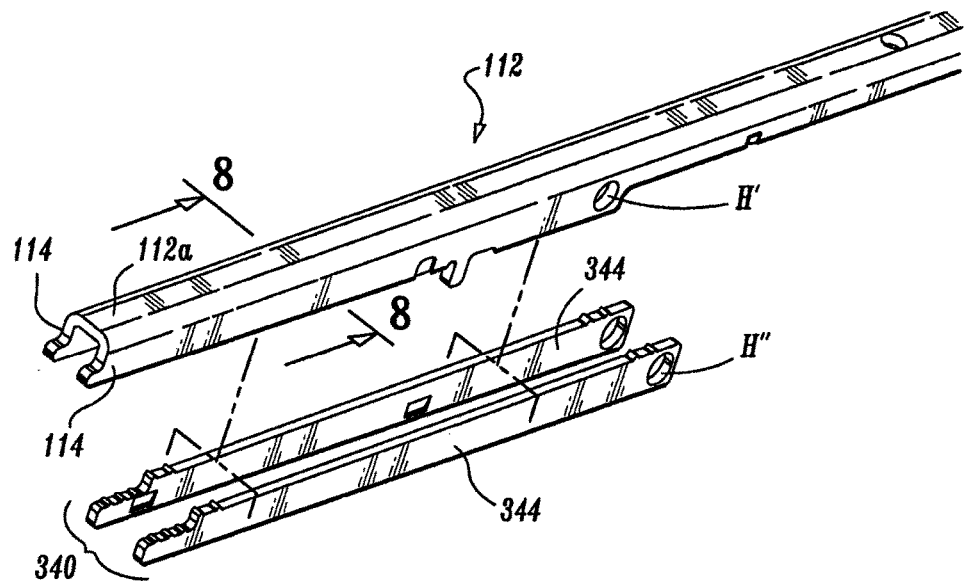
FIG. 7 is a bottom perspective view, with parts separated, of the distal end of an anvil half-section, in accordance with another embodiment of the present disclosure.
Figure 8:
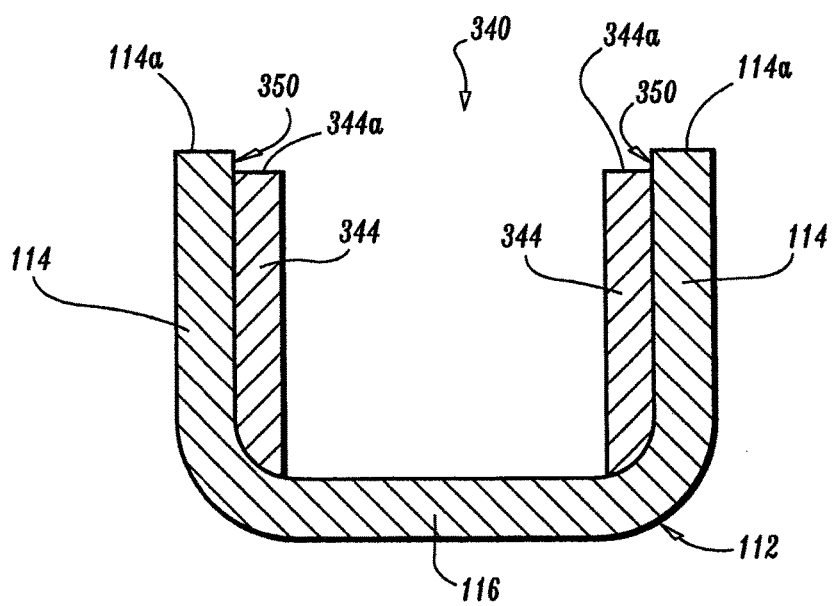
FIG. 8 is a transverse cross-sectional view of a portion of the distal end of a channel member of the assembled parts of the anvil half section of FIG. 8, as would be seen along section line 8-8 of FIG. 7.

Preferably, as seen in FIG. 7, each reinforcing rib 344 includes a through hole H" at or near proximal end 344c thereof which aligns with and/or is in registration with a slot or hole H' formed in each side wall 114 of channel member 112 at or adjacent intermediate point 112c of channel member 112. Preferably, a pin or cam member 400 (see FIGS. 2, 18-21 and 23) extends through aligned holes H' of channel member 112 and through holes H" of each reinforcing rib 344, and in turn extend transversely through side walls 114 of channel member 112 of anvil half-section 104. Such a cam member 400 and the manner in which it operates is disclosed in International Appl. Ser. No. PCT/US03/08342 filed on Mar. 13, 2003, the entire contents of which are incorporated herein by reference.

Preferably, as best seen in FIG. 23, through-hole H" of each reinforcing rib 344 has a diameter "D1" and the portion of cam 400 extending through through-hole H" of each reinforcing rib 344 has a diameter "D2" which is less than diameter "D1" of through-hole H". In a preferred embodiment, diameter "D1" of through-hole H" is about 0.203 inches and diameter "D2" of the portion of cam 400 extending through-hole H" is about 0.200 inches thereby defining a reveal of about 0.003 inches.

In operation, when tissue having a relatively smaller thickness is clamped between distal ends 104a, 102a of anvil half-section 104 and cartridge receiving half-section 102, distal end 104a of anvil half-section 104 will tend to deflect an amount sufficient for tissue gap "G" to have a substantially uniform dimension from the proximal end to the distal end thereof.

When or as tissue having a relatively larger thickness is clamped between distal ends 104a, 102a of anvil half-section 104 and cartridge receiving half-section 102, deflection control system 640 causes distal end 104a of anvil half-section 104 to undergo a two-stage deflection. The rate of deflection is established when distal end 112a of channel member 112 and distal end 344b of reinforcing ribs 344 are loaded with a force. When apparatus 100 is clamped onto relatively thin tissue, the rate of deflection will be at a maximum to allow the tissue gap "G" to be set relatively quickly. This maximum rate of deflection is attained from the existent of the reveal between through-hole H" of each reinforcing rib 344 and the portion of cam 400 extending through through-hole H" of each reinforcing rib 344. When apparatus 100 is clamped onto relatively thicker tissue, the rate of deflection needs to be reduced and/or at a minimum in order to maintain the proper tissue gap "G" for staple formation. This reduced rate of deflection is attained as a result of the size of the reveal between through-hole H" of each reinforcing rib 344 and the portion of cam 400 extending through through-hole H" of each reinforcing rib 344 being reduced to zero. As will be described in greater detail below, once the reveal is reduced to zero the rate of deflection is decreased to a desired and/or optimum rate.

In the first stage of deflection the deflection force acts on edge surfaces 114a of side walls 114 of channel member 112 resulting in distal end 104a of anvil half-section 104 undergoing an initial rate of deflection in direction "Y". Since each reinforcing rib 344 is welded to side walls 114, each reinforcing rib 344 travels with channel member 112. Moreover, since distal end 104a of anvil half-section 104 is urged in the direction of arrow "Y", as distal end 344b of each reinforcing rib 344 is displaced in direction "Y", proximal end 344c of each reinforcing rib 344 is displaced in a direction opposite to direction "Y" thereby engaging an upper portion of the rim 404 of through-hole H" formed in each reinforcing rib 344 towards an upper portion 402 of cam 400 extending through-hole H" and minimizing the reveal that exists therebetween. This first stage of deflection continues until the reveal between upper portion of rim 404 of through-hole H" and upper portion 402 of cam 400 extending therethrough is reduced to zero. Once the reveal between upper portion of rim 404 of through-hole H" and upper portion 402 of cam 400 is reduced to zero and upper portion of rim 404 of through-hole H" contacts with upper portion 402 of cam 400 extending therethrough, distal end 104a of anvil half-section 104 undergoes a second stage of deflection.

In the second stage of deflection, deflection control system 640 causes distal end 104a of anvil half-section 104 to undergo a rate of deflection which is less than the initial rate of deflection. In operation, since upper portion 404 of hole H" is in contact with upper portion 402 of cam 400 extending therethrough, proximal end 344c is prevented from moving further in the direction opposite to arrow "Y". Accordingly, since distal end 344b of reinforcing ribs 344 are urged in the direction of arrow "Y", the prevention of movement of proximal end 344c of reinforcing ribs 344 in the direction opposite to direction "Y" prevents movement of distal end 344b of reinforcing ribs 344 in direction "Y", thereby reinforcing distal end 104a of anvil half-section 104 and reducing the rate of deflection thereof.

Deflection control system 640 in effect prevents the distal end of tissue gap "G" from having a reverse tapered configuration (i.e., the distal end having a larger height than the proximal end).

It is contemplated that surgical stapling apparatus 100 can be provided with directionally biased formable staples and/or be provided with anvil pockets for forming the staples in a predetermined manner. Such a surgical stapling apparatus is disclosed in U.S. application Ser. No. 09/693,379 filed on Oct. 20, 2000, entitled "Directionally Biased Staples and Cartridge Having Directionally Biased Staples", the entire contents of which are incorporated herein by reference.

In each of the embodiments disclosed herein, the deflection control systems reduce the degree and/or amount of deflection of distal end 112a of channel member 112, and in turn the degree and/or amount of deflection of distal end 104a of anvil half-section 104, of surgical fastener applying apparatus 100, as compared to a surgical fastener applying apparatus not including a deflection control system according to any of the embodiments disclosed herein.

It will be understood that the particular embodiments described above are only illustrative of the principles of the disclosure, and that various modifications can be made by those skilled in the art without departing from the scope and spirit of the disclosure.

What is claimed:

1. A surgical fastener applying apparatus, comprising:
   an anvil half-section defining a longitudinal axis and a tissue contacting surface, the anvil half-section including a proximal end and a distal end;
   a cartridge receiving half-section mechanically coupled to the anvil half-section; and a multi-stage deflection control system mechanically coupled to the anvil half-section, the deflection control system having more than one plate and a pin member securing the more than one plate to the distal end of the anvil half-section, to reinforce the distal end of the anvil half-section upon application of a force thereto, such that a rate of deflection of the distal end of the anvil half-section changes.

2. The surgical fastener applying apparatus according to claim 1, wherein the more than one plate comprises a first plate having a slot and a second plate having a slot, the pin being disposed in the slot of the first plate and the slot of the second plate.

3. The surgical fastener applying apparatus according to claim 2, wherein the first plate and second plate are configured so that the rate of deflection progressively decreases during compression of tissue positioned between the anvil half-section and the cartridge receiving half-section.

4. The surgical fastener applying apparatus of claim 3, wherein the pin member includes:
   a body portion with a first end fixedly secured to the anvil half-section;
   a second end extending through the slots formed in the first and second plates of the reinforcing member; and
   a head secured to the second end, the head defining a transverse dimension larger than a corresponding transverse dimension of at least one of the slots formed in the first and second plates.

5. The surgical fastener applying apparatus according to claim 1, wherein the first plate has a proximal end, a distal end, and the slot of the first plate is formed in the distal end thereof and has a length, the second plate has a proximal end, a distal end, and the slot of the second plate is formed in the distal end thereof and has a length, the length of the slot of the second plate being different than the length of the slot of the first plate.

6. The surgical fastener applying apparatus according to claim 5, wherein the pin is configured and dimensioned for receipt in the slot of the first plate and in the slot of the second plate such that the first plate and the second plate are slidably secured to the distal end of the anvil half-section.

7. The surgical fastener applying apparatus of claim 6, wherein the length of the slot formed in the second plate is greater than the length of the slot formed in the first plate.

8. The surgical fastener applying apparatus of claim 1, wherein the slot of the first plate and the slot of the second plate extends in substantially parallel to the longitudinal axis.

* * * * *